(12) United States Patent
Sinha et al.

(10) Patent No.: US 8,455,440 B2
(45) Date of Patent: Jun. 4, 2013

(54) COMBINATION ANTICOAGULANT THERAPY WITH A COMPOUND THAT ACTS AS A FACTOR XA INHIBITOR

(75) Inventors: Uma Sinha, San Francisco, CA (US); Stanley J. Hollenbach, South San Francisco, CA (US); Patrick Andre, San Mateo, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/213,912

(22) Filed: Aug. 19, 2011

(65) Prior Publication Data

US 2012/0046230 A1 Feb. 23, 2012

Related U.S. Application Data

(63) Continuation of application No. 12/101,644, filed on Apr. 11, 2008, now abandoned.

(60) Provisional application No. 60/911,852, filed on Apr. 13, 2007.

(51) Int. Cl.
*A61K 38/57* (2006.01)

(52) U.S. Cl.
USPC ........ 514/14.4; 514/13.7; 514/14.9; 514/183; 514/185; 514/188; 424/94.64

(58) Field of Classification Search
None
See application file for complete search history.

(56) References Cited

U.S. PATENT DOCUMENTS

| | | | |
|---|---|---|---|
| 6,376,515 B2 | 4/2002 | Zhu et al. | |
| 6,794,412 B1 | 9/2004 | Wong | |
| 6,835,739 B2 | 12/2004 | Zhu et al. | |
| 6,844,367 B1 | 1/2005 | Zhu et al. | |
| 7,018,990 B2 * | 3/2006 | Wong et al. | 514/161 |
| 7,022,695 B2 | 4/2006 | Zhu et al. | |
| 7,285,565 B2 | 10/2007 | Zhu et al. | |
| 7,312,235 B2 | 12/2007 | Zhu et al. | |
| 7,314,874 B2 | 1/2008 | Zhu et al. | |
| 7,342,013 B2 | 3/2008 | Zhu et al. | |
| 7,618,955 B2 | 11/2009 | Verbeuren et al. | |
| 7,727,981 B2 | 6/2010 | Zhu et al. | |
| 7,767,697 B2 | 8/2010 | Song et al. | |
| 2002/0002183 A1 | 1/2002 | Zhu et al. | |
| 2003/0114371 A1 | 6/2003 | Feder et al. | |
| 2003/0211075 A1 | 11/2003 | Thorpe et al. | |
| 2004/0191757 A1 | 9/2004 | Maher et al. | |
| 2004/0248099 A1 | 12/2004 | Goppel et al. | |
| 2005/0089473 A1 | 4/2005 | Black et al. | |
| 2006/0100193 A1 | 5/2006 | Zhu et al. | |
| 2007/0112039 A1 | 5/2007 | Grant et al. | |
| 2007/0185092 A1 | 8/2007 | Zhu et al. | |
| 2007/0259924 A1 | 11/2007 | Song et al. | |
| 2008/0153876 A1 | 6/2008 | Sinha et al. | |
| 2008/0279845 A1 | 11/2008 | Conley et al. | |
| 2008/0293704 A1 | 11/2008 | Jia et al. | |
| 2009/0186810 A1 | 7/2009 | Zwaal et al. | |
| 2010/0056564 A1 | 3/2010 | Cloarec-Blanchard et al. | |

FOREIGN PATENT DOCUMENTS

| | | |
|---|---|---|
| EP | 1908481 | 4/2008 |
| WO | WO 95/29189 | 11/1995 |
| WO | WO 00/32579 | 6/2000 |
| WO | WO 02/10159 | 2/2002 |
| WO | WO 02/038186 | 5/2002 |
| WO | WO 03/045912 | 6/2003 |
| WO | WO 2005/097784 | 10/2005 |
| WO | WO 2006/032384 | 3/2006 |
| WO | WO 2006/097220 | 9/2006 |
| WO | WO 2006/137510 | 12/2006 |
| WO | WO 2007/056517 | 5/2007 |
| WO | WO 2008/057972 | 5/2008 |

OTHER PUBLICATIONS

International Search Report of PCT/US/2008/004760, dated Mar. 4, 2009.
Van Raalte, D. et al., "Peroxisome proliferator-activated receptor (PPAR)-alpha: A pharmacological target with a promising future," Pharmaceutical Research (Dordrecht), vol. 21, No. 9 (2004), pp. 1531-1538, XP002516226.

* cited by examiner

*Primary Examiner* — Michael Szperka
(74) *Attorney, Agent, or Firm* — Foley & Lardner LLP

(57) ABSTRACT

The present invention is directed to methods of using combination therapies containing [2-({4-[(dimethylamino)iminomethyl]phenyl}carbonylamino)-5-methoxyphenyl]-N-(5-chloro(2-pyridyl))carboxamide for the treatment of thrombotic disease(s) and pharmaceutical compositions thereof.

24 Claims, 2 Drawing Sheets

COMBINATION ANTICOAGULANT THERAPY WITH A COMPOUND THAT ACTS AS A FACTOR XA INHIBITOR

CROSS REFERENCE TO RELATED APPLICATIONS

This application is a continuation of U.S. application Ser. No. 12/101,644, filed Apr. 11, 2008 now abandoned, which claims the benefit under 35 U.S.C. §119(e) of U.S. Provisional Patent Application No. 60/911,852, filed on Apr. 13, 2007, both of which are hereby incorporated by reference in their entirety.

FIELD OF INVENTION

The present invention relates generally to novel pharmaceutical compositions and methods for treating thrombotic diseases using a combination of a factor Xa inhibitor and other agents.

BACKGROUND OF THE INVENTION

This invention is particularly concerned with blood coagulation and ways in which coagulation assists in maintaining the integrity of mammalian circulation after injury, inflammation, disease, congenital defect, dysfunction or other disruption. Clot formation involves the conversion of fibrinogen to fibrin which polymerizes into a network to restore hemostasis after injury. A similar process results in occluded blood vessels in thrombotic diseases. The conversion of fibrinogen to fibrin is catalyzed by thrombin, the end product of a series of reactions in the blood coagulation cascade. Factor Xa, a serine protease, is the sole enzyme responsible for sustained thrombin formation in the vasculature. Thus, inhibition of factor Xa is considered to be an efficient anticoagulant strategy.

U.S. Pat. Nos. 6,376,515 B2 and 6,835,739 B2, the contents of which are incorporated herein by reference, disclose a specific factor Xa inhibitor compound, [2-({4-[(dimethylamino)iminomethyl]phenyl}carbonylamino)-5-methoxyphenyl]-N-(5-chloro(2-pyridyl))carboxamide (Compound A), which has the following structure:

Compound A

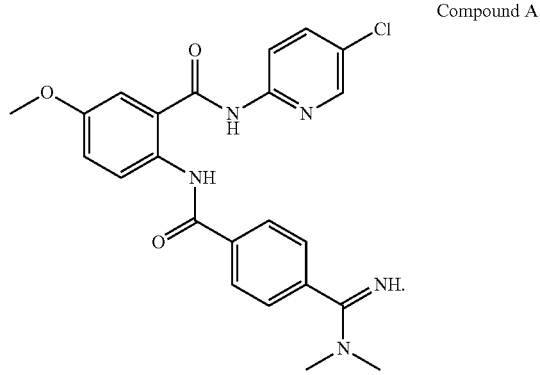

Since treatment for diseases such as acute coronary syndromes might require co-administration of an anticoagulant agent and an antiplatelet agent, a combination would allow for increased efficacy as well as superior patient compliance during chronic treatment. However, some current anticoagulants therapies are not suitable for combination therapy. For example, warfarin, a currently available anticoagulant for chronic use, requires dose titration using international normalized ratio (INR) clotting assays to avoid excessive blood thinning and the risk of bleeding. Therefore it cannot be used as a combination with an antiplatelet agent at a fixed dose. Further, while some anticoagulant agents and antiplatelet agents may be suitable for combination therapy, they do not provide sufficient therapeutic benefit. For example, a recent clinical study examined patients on fondaparinux (an anticoagulant agent) and either aspirin or clopidogrel. The patients continued to experience thrombotic events over the course of the study. (Fifth Organization to Assess Strategies in Acute Ischemic Syndromes Investigators, et al, *N. Engl. J. Med.* 2006, 354(14):1464-76).

Thus, there is a need for combination therapies that combine a fixed dose of anticoagulant agent with an antiplatelet agent that have enhanced efficacy. Further, there is a need for combination therapies for patients having thrombotic disease(s) with other co-existing conditions, such as high blood pressure or inflammation.

SUMMARY OF THE INVENTION

This invention provides methods and pharmaceutical compositions of combined therapies comprising a factor Xa inhibitor, having the following structure:

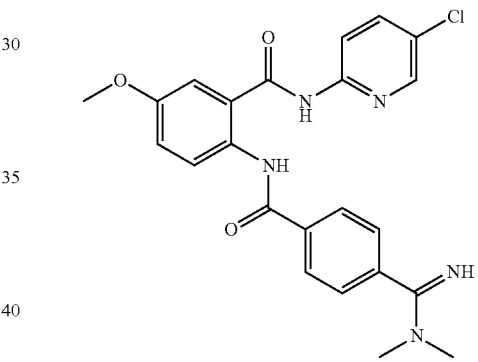

which has the chemical name, [2-({4-[(dimethylamino)iminomethyl]phenyl}carbonylamino)-5-methoxyphenyl]-N-(5-chloro(2-pyridyl))carboxamide and is referred to throughout as "Compound A".

This compound has been shown to have the ability to treat conditions associated with undesired thrombosis. A patient undergoing treatment for undesired thrombosis are often in need of receiving additional cardiac and/or vascular therapy.

Compound A has been shown to have predictable levels of anticoagulation as measured by pharmacodynamic assays. This is more thoroughly described in Examples 2 and 3. Thus, it is contemplated that Compound A can surprisingly and unexpectedly be used in a fixed, non-dose-titrated manner in combination with other therapeutic agents for the treatment of thrombotic disease. It is further contemplated that Compound A when provided in combination with certain other therapeutic agents shows a synergistic effect illustrated by superior efficacy or safety profile.

The present invention provides novel methods for treating a condition in a mammal characterized by undesired thrombosis, comprising administering to said mammal a therapeutically effective amount of the Compound A, [2-({4-[(dimethylamino)iminomethyl]phenyl}carbonylamino)-5-methoxyphenyl]-N-(5-chloro(2-pyridyl))carboxamide, or a pharmaceutically acceptable salt thereof, and a therapeutically effective amount of another therapeutic agent. The other therapeutically effective agent is selected from an antiplatelet agent, an anticoagulant agent, an inflammatory agent, a blood pressure lowering agent and combinations thereof. In one embodiment, Compound A and the other therapeutic agent can be combined with another agent selected from a thrombin inhibitor, a thrombolytic agent, an antiarrhythmic agent, a cholesterol or triglyceride agent and combinations thereof.

The invention is also directed to pharmaceutical compositions comprising a compound of the following formula:

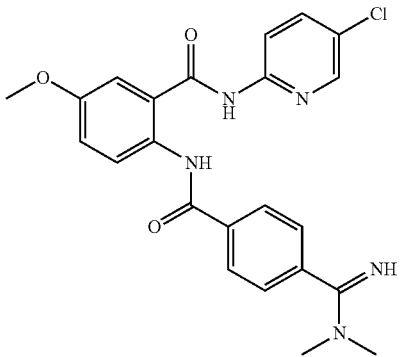

which has the chemical name, [2-({4-[(dimethylamino)iminomethyl]phenyl}carbonylamino)-5-methoxyphenyl]-N-(5-chloro(2-pyridyl))carboxamide and another therapeutic agent, including, an antiplatelet agent, an anticoagulant agent, an inflammatory agent, and combinations thereof.

DETAILED DESCRIPTION OF THE INVENTION

Figure 1:
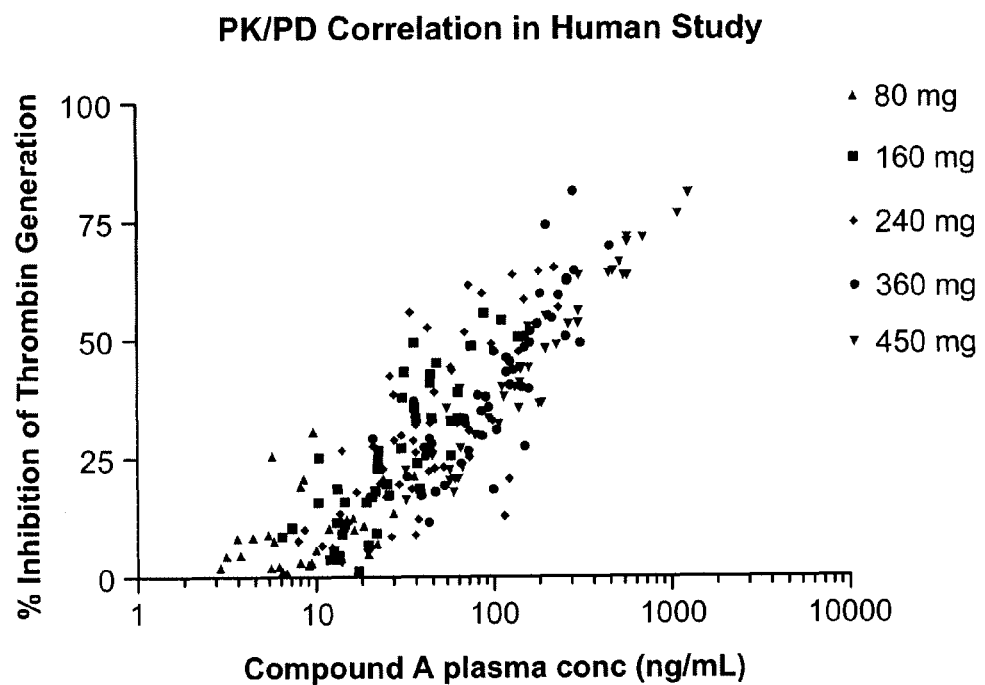
FIG. 1 and FIG. 2 show the correlation of Compound A plasma concentration and inhibition of thrombin generation in human studies.

This invention relates to methods and compositions for treating a condition in a mammal characterized by undesired thrombosis using a combination of Compound A with another therapeutic agent. Prior to describing this invention in more detail, the following terms will first be defined.

I. DEFINITIONS

It is to be noted that as used herein and in the claims, the singular forms "a," "an" and "the" include plural referents unless the context clearly dictates otherwise. Thus, for example, reference to "a pharmaceutically acceptable carrier" in a composition includes two or more pharmaceutically acceptable carriers, and so forth.

It must be further noted that the classification of certain therapeutic agents based on their intended use or mechanisms of action is based on the general knowledge of a person skilled in the art and for classification purposes only. The purported mechanisms are not intended to be used as a limitation for the therapeutic agents unless the context clearly dictates otherwise. Some therapeutic agents may act through two or more mechanisms or are able to be used to treat two or more conditions. It is also to be understood that the particular agents given in each categories are for examples only and are not intended to limit the scope of the present invention.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The invention provides methods of treating a condition in a mammal characterized by undesired thrombosis using a combination therapy having Compound A and other therapeutic agents. "Treat" or "treating" or "treatment" of a disease or condition in a patient refers to 1) preventing the disease or condition from occurring in a mammal, in particular, a mammal who is predisposed or does not yet display symptoms of the disease or condition; 2) inhibiting the disease or condition or arresting its development; or 3) ameliorating or causing regression of the disease or condition.

The term "mammal" includes organisms which express factor Xa. Examples of mammals include mice, rats, cows, sheep, pigs, goats, horses, bears, monkeys, dogs, cats and, preferably, humans. Transgenic organisms which express factor Xa are also included in this definition.

The term "a condition characterized by undesired thrombosis" refers to any of, but is not limited to the following: (a) thrombotically mediated acute coronary syndrome including myocardial infarction, unstable angina, refractory angina, occlusive coronary thrombus occurring post-thrombolytic therapy or post-coronary angioplasty, (b) thrombotically mediated cerebrovascular syndrome including embolic stroke, thrombotic stroke or transient ischemic attacks, (c) thrombotic syndrome occurring in the venous system including deep venous thrombosis or pulmonary embolus occurring either spontaneously or in the setting of malignancy, surgery or trauma, (d) coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) thrombotic complications associated with extracorporeal circulation (e.g. renal dialysis, cardiopulmonary bypass or other oxygenation procedure, plasmapheresis), (f) thrombotic complications associated with instrumentation (e.g. cardiac or other intravascular catheterization, intra-aortic balloon pump, coronary stent or cardiac valve), and (g) those involved with the fitting of prosthetic devices.

"Therapeutically effective amount" means an amount of Compound A or the co-administered therapeutic agent of the present invention that is effective to treat a target disease or condition when administered in combination. In some embodiments, therapeutically effective amount is the amount of each agent in the combination that is sufficient for the combination therapy to be effective in reducing, treating or preventing undesired thrombosis. It is contemplated that in some embodiments, the therapeutically effective amounts of the one or all agents in the combination therapy are lower than the amounts needed to produce the same level of effect when the agents are used alone. The therapeutically effective amount will vary depending upon the specific combination, the subject and disease condition being treated, the weight and age of the subject, the severity of the disease condition, the dosing regimen to be followed, timing of administration, the manner of administration and the like, all of which can be determined readily by one of ordinary skill in the art.

"Sub-therapeutic dosage" refers to a dosage that is lower than the optimal dosage for a therapeutic agent when used as a single agent, but when used in the combinations described herein, provides a therapeutic result.

"Antiplatelet agents" or "platelet inhibitors" are agents that block the formation of blood clots by preventing the aggregation of platelets. There are several classes of antiplatelet agents based on their activities, including, GP IIb/IIIa antagonists, such as abciximab (ReoPro®), eptifibatide (Integrilin®), and tirofiban (Aggrastat®); $P2Y_{12}$ receptor antagonists, such as clopidogrel (Plavix®), ticlopidine (Ticlid®), cangrelor, ticagrelor (also known as AZD 6140), and prasugrel (also known as CS-747 and LY640315); phosphodiesterase III (PDE III) inhibitors, such as cilostazol (Pletal®), dipyridamole (Persantine®) and Aggrenox® (aspirin/extended-release dipyridamole); thromboxane synthase inhibitors, such as furegrelate, ozagrel, ridogrel and isbogrel; thromboxane A2 receptor antagonists, such as ifetroban, ramatroban, terbogrel, Servier S 18886 (having the chemical name of 3-{6-[(4-chlorophenylsulfonyl)amino]-2-methyl-5, 6,7,8-tetrahydronaphth-1-yl}propionic acid, by de Recherches Internationales Servier, Courbevoie, France); thrombin receptor antagonists, such as SCH530348 (having the chemical name of ethyl (1R,3aR,4aR,6R,8aR,9S,9aS)-9-((E)-2-(5-(3-fluorophenyl)pyridin-2-yl)vinyl)-1-methyl-3-oxododecahydronaphtho[2,3-C]furan-6-ylcarbamate (described in US20040192753A1 and US2004/0176418A1, by Schering Plough Corp., New Jersey, USA) p selectin inhibitors, such as Way-197697 (also known as PSI-697, having the chemical name of 2-(4-chlorobenzyl)-3-hydroxy-7,8,9,10-tetrahydrobenzo[H]quinoline-4-carboxylic acid) or Way-290421 (having the chemical name of 2-(4-chlorophenyl)cyclopropyl)-3-hydroxy-8-(trifluoromethyl)quinoline-4-carboxylic acid, by Wyeth, New Jersey, USA); and non-steroidal anti-inflammatory drugs (NSAIDS), such as acetylsalicylic acid (Aspirin®), ibuprofen (Advil®, Motrin®), naproxen (Aleve®, Naprosyn®), sulindac (Clinoril®), indomethacin (Indocin®), mefenamate, droxicam, diclofenac (Cataflam®, Voltaren®), sulfinpyrazone (Anturane®), and piroxicam (Feldene®). Among the NSAIDS, acetylsalicylic acid (ASA) and piroxicam are preferred. Beta blockers and calcium channel blockers, which are described below, also have a platelet-inhibiting effect.

"Anticoagulant agents" or "anticoagulants" are agents that prevent blood clot formation. Examples of anticoagulant agents include, but are not limited to, specific inhibitors of thrombin, factor IXa, factor Xa, factor XIa, factor XIIa or factor VIIa, heparin and derivatives, vitamin K antagonists, and anti-tissue factor antibodies. Examples of specific inhibitors of thrombin include hirudin, bivalirudin (Angiomax®), dabigatran (Pradaxa®), argatroban and lepirudin (Refludan®). Examples of heparin and derivatives include unfractionated heparin (UFH), low molecular weight heparin (LMWH), such as enoxaparin (Lovenox®), dalteparin (Fragmin®), and danaparoid (Organan®); and synthetic pentasaccharide, such as fondaparinux (Arixtra®). Examples of vitamin K antagonists include warfarin (Coumadin®), phenocoumarol, acenocoumarol (Sintrom®), clorindione, dicumarol, diphenadione, ethyl biscoumacetate, phenprocoumon, phenindione, and tioclomarol.

"Injectable anticoagulants" are anticoagulant agents that are administered to a mammal through injections. Examples of injectable anticoagulants are unfractionated heparin, low molecular weight heparins, and synthetic pentasaccharides.

"Anti-inflammatory agents" are agents used for the treatment of inflammatory conditions or diseases. Examples of anti-inflammatory agents include non-steroidal anti-inflammatory agents, acetylsalicylic acid (Aspirin®), piroxicam (Feldene®), indomethacin (Indocin®), mesalamine (Pentasa®, Rowasa®, Asacol®), sulfasalazine (Azulfidine®), methotrexate (Rheumatrex®), leflunomide (Arava®); tumor necrosis factor antagonists, such as adalimubab (Humira®), etanercept (Enbrel®), and infliximab (Remicade®); interleukin 1 receptor antagonist, such as anakinra (Kineret®); cyclooxygenase-2 inhibitors and rheumatoid arthritis agents.

"Blood pressure lowering agents" or "anti-hypertensive agents" are agents that are used to treat hypertension, a condition in which the blood pressure is chronically higher than normal. Persistent hypertension is one of the risk factors for strokes, heart attacks, heart failure and arterial aneurysm, and is a leading cause of chronic renal failure. Examples of blood pressure lowering agents include calcium channel blockers, such as verapamil (Calan®, Isoptin®), diltiazem (Cardizem®), amlodipine (Norvasc®), and nifedipine (Adalat®, Procardia®); diuretics, such as hydrochlorothiazide, metolazone (Zaroxolyn®), furosemide (Lasix®), bumetanide (Bumex®), spironolactone (Aldactone®), and eplerenone (Inspra®); beta-adrenergic antagonists (beta blockers), such as metoprolol (Lopressor®), nadolol (Corgard®), pindolol (Visken®) propranolol (Inderal®), timolol (Blocadren®), and Betaxolol (Betoptic®); angiotensin converting enzyme (ACE) inhibitors, such as captopril (Capoten®), benazepril (Lotensin®), enalapril (Vasotec®), lisinopril (Prinivil®, Zestril®), fosinopril (Monopril®), ramipril (Altace®), perindopril (Aceon®), quinapril (Accupril®), moexipril (Univasc®), and trandolapril (Mavik®); angiotensin 2 receptor antagonists, such as candesartan cilexetil (Atacand®), irbesartan (Avapro®), losartan (Cozaar®), telmisartan (Micardis®), and valsartan (Diovan®); alpha-1-adrenergic antagonists, such as doxazosin (Cardura®), prazosin (Minipress®), and terazosin hydrochloride (Hytrin®); combined alpha/beta-adrenergic antagonists, such as labetalol (Normodyne®, Trandate®) and carvedilol (Coreg®); adrenergic neuron blocking agents, such as guanethidine (Ismelin®) and reserpine (Serpasil®); central nervous system-acting antihypertensives, such as clonidine (Catapres®), methyldopa (Aldomet®), and guanabenz (Wytensin®); and direct vasodilators, such as nitroprusside (Nipride®), diazoxide (Hyperstat IV®), hydralazine (Apresoline®), minoxidil (Loniten®), and verapamil (Calan®, Verelan®).

"Thrombolytic agents" or "fibrinolytic agents" are agents that are able to break down an existing blood clot. Examples of thrombolytic agents include natural and recombinant tissue plasminogen activators, anistreplase, dual and single chain urokinases (urokinase-type plasminogen activators (uPA)), streptokinase, tenecteplase (TNK), lanoteplase (nPA), factor VIIa inhibitors, PAI-1 inhibitors (inactivators of tissue plasminogen activator inhibitors), and alpha2 antiplasmin inhibitors.

"Antiarrhythmic agents" are agents that are used to treat disorders of the heart rate and rhythm. Examples of antiarrhythmic agents include Class I agents which interfere with the sodium channel, such as quinidine (Apo-Quinidine®), procainamide (Pronestyl®), propafenone (Rythmol®), lidocaine (Xylocalne®) and disopyramide (Norpace®);

Class II agents which are beta blockers, such as carvedilol (Coreg®) and propranolol (Inderal®); Class III agents which block the potassium channels, such as sotalol (Betapace®), dofetilide (Tikosyn®), amiodarone (Cordarone®), azimilide and ibutilide (Corvert®); Class IV agents which are calcium channel blockers, such as verapamil (Calan®, Verelan®) and diltiazem (Cardizem®) and cardiac glycosides, such as digoxin (Lanoxin®); and angiotensin 2 receptor antagonists.

"Cholesterol and triglyceride lowering agents" are agents used to lower the amount of cholesterol or lipid present in the blood. Abnormally high levels of cholesterol are associated with atherosclerosis, which is a major cause of coronary heart diseases and other forms of cardiovascular disease. Examples of cholesterol lowering agents include resins (bill acid binders or bile acid sequestrants), such as cholestyramine (Questran®, Prevalite®, Lo-Cholest®), colestipol (Colestid®), colesevelam (WelChol®); fibrates, such as ciprofibrate (Modalim®), gemfibrozil (Lopid®), fenofibrate (TriCor®) and bezafibrate (Bezalip®); statins, such as atorvastatin (Lipitor®), fluvastatin (Lescol®), lovastatin (Mevacor®, Altocor®), itavastatin (also known as, NK-104 or nisvastatin or nisbastatin), mevastatin (Capactin®), pitavastatin (Livalo®, Pitava®), pravastatin (Pravachol®, Lipostat®), rosuvastatin (Crestor®), and simvastatin (Zocor®); cholesterol absorption inhibitors, such as ezetimibe (Zetia®); squalene synthetase inhibitors; cholesterol ester transfer protein inhibitors, such as torcetrapib; niacin and omega-3 fatty acid.

The term "pharmaceutically acceptable salts" is meant to include salts of the active compounds which are prepared with relatively nontoxic acids or bases, depending on the particular substituents found on the particular therapeutic agents described herein. When therapeutic agents described in the invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When therapeutic agents described in the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", *Journal of Pharmaceutical Science*, 1977, 66:1-19). Certain specific therapeutic agents contain both basic and acidic functionalities that allow the compounds to be converted into either base or acid addition salts.

Certain preferred salt forms for compound A are disclosed in U.S. Patent Publication US2007/0112039, which claims the benefit of U.S. Provisional Application Ser. No. 60/735,224 filed on Nov. 8, 2005, both of which are incorporated herein by reference. In particular, these two patent applications disclose that Compound A forms a salt with an acid. The acid is preferably selected from the group consisting of hydrochloric, lactic, maleic, phenoxyacetic, propionic, succinic, adipic, ascorbic, camphoric, gluconic, phosphic, tartric, citric, methanesulfonic, fumaric, glycolic, naphthalene-1,5-disulfonic, gentisic and benzenesulfonic. In one embodiment, the acid is selected from the group consisting of hydrochloric, lactic, maleic, phenoxyacetic, propionic, and succinic. In another embodiment, the acid is maleic acid. When referring to a salt form of Compound A, the ion form of the salt is used. For example, if Compound A forms a salt with maleic acid, the salt is referred to as the maleate salt. One embodiment of the maleate salt of Compound A exists as Formula I

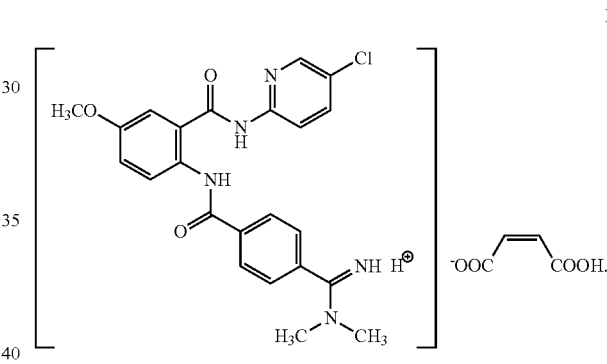

Further, the salt of Formula I may exist in a crystalline polymorph as disclosed in U.S. Patent Publication US2007/0112039. One crystalline polymorph form of Formula I exhibits a powder X-ray diffraction pattern having at least four and preferably eight of the following approximate characteristic peak locations: 4.9, 9.7, 13.8, 14.1, 15.2, 17.6, 18.5, 20.8, 21.6, 22.7, 24.1, 26.3, 26.8 degrees 2θ. In a more preferred crystalline polymorph form, the powder X-ray diffraction pattern has approximate characteristic peak locations of 4.9, 9.7, 11.8, 13.8, 14.1, 15.2, 17.6, 18.5, 19.9, 20.8, 21.6, 22.7, 24.1, 25.0, 26.3, 26.8 degrees 2θ.

The neutral forms of the therapeutic agents may be regenerated by contacting the salt with a base or acid and isolating the parent therapeutic agent in the conventional manner. The parent form of the therapeutic agent differs from the various salt forms in certain physical properties, such as solubility in polar solvents, but otherwise the salts are equivalent to the parent form for the purposes of the present invention.

In addition to salt forms, certain therapeutic agents are in a prodrug form. Prodrugs of the therapeutic agents are those compounds that readily undergo chemical changes under physiological conditions to provide the compound having therapeutic activities. Additionally, prodrugs can be converted to the active compound by chemical or biochemical methods in an ex vivo environment. For example, prodrugs can be slowly converted to the active compound described in the invention when placed in a transdermal patch reservoir with a suitable enzyme or chemical reagent.

Certain therapeutic agents described in the invention can exist in unsolvated forms as well as solvated forms, including hydrated forms. In general, the solvated forms are equivalent to unsolvated forms and are intended to be encompassed within the scope of the present invention. Certain therapeutic agents may exist in multiple crystalline or amorphous forms. In general, all physical forms are equivalent for the uses contemplated by the present invention and are intended to be within the scope of the present invention.

"Pharmaceutically acceptable carriers" refers to any diluents, excipients, or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in *Remington's Pharmaceutical Sciences*, Mack Publishing Company, a standard reference text in this field. They are preferably selected with respect to the intended form of administration, that is, oral tablets, capsules, elixirs, syrups and the like, and consistent with conventional pharmaceutical practices.

II. DETAILED DESCRIPTION OF THE EMBODIMENTS

The present invention provides novel methods for treating a condition in a mammal characterized by undesired thrombosis, comprising administering to said mammal a therapeutically effective amount of the Compound A, having the following formula:

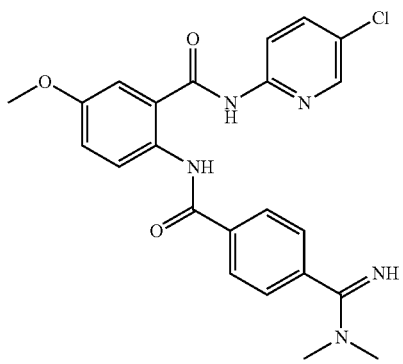

and the chemical name [2-({4-[(dimethylamino)iminomethyl]phenyl}carbonylamino)-5-methoxyphenyl]-N-(5-chloro(2-pyridyl))carboxamide, or a pharmaceutically acceptable salt thereof, and a therapeutically effective amount of another therapeutic agent. The other therapeutically effective agent is selected from an antiplatelet agent, an anticoagulant agent, an inflammatory agent, a blood pressure lowering agent and combinations thereof. In one embodiment, Compound A and the other therapeutic agent can be combined with another agent selected from a thrombin inhibitor, a thrombolytic agent, an antiarrhythmic agent, a cholesterol or triglyceride agent and combination thereof.

Accordingly, in a first group of embodiments, the invention provides a method for treating a condition in a mammal characterized by undesired thrombosis comprising administering to said mammal a therapeutically effective amount of:

(1) [2-({4-[(dimethylamino)iminomethyl]phenyl}carbonylamino)-5-methoxyphenyl]-N-(5-chloro(2-pyridyl))carboxamide, or a pharmaceutically acceptable salt thereof; and (2) an antiplatelet agent.

In some embodiments of the first group, the antiplatelet agent is a GP IIb/IIIa receptor antagonist.

In other embodiments of the first group, the antiplatelet agent is a $P2Y_{12}$ receptor antagonist.

In still other embodiments of the first group, the antiplatelet agent is a phosphodiesterase III inhibitor.

In other embodiments of the first group, the antiplatelet agent is a thromboxane synthase inhibitor.

In other embodiments of the first group, the antiplatelet agent is a thromboxane A2 receptor antagonist.

In other embodiments of the first group, the antiplatelet agent is a thrombin receptor antagonist.

In other embodiments of the first group, the antiplatelet agent is an inhibitor of p selectin.

In some embodiments of the first group, the antiplatelet agent is selected from the group consisting of: abciximab, eptifibatide, tirofiban, acetylsalicylic acid, cangrelor, ticagrelor, clopidogrel, ticlopidine, prasugrel, dipyridamole, aggrenox, SCH530348, PSI-697, ifetroban, cilostazol, isbogrel, furegrelate, ramatroban, ridogrel, terbogrel, Servier S 18886 and ozagrel.

In some embodiments of the first group, the antiplatelet agent is eptifibatide.

In some embodiments of the first group, the antiplatelet agent is clopidogrel.

In a second group of embodiments, the invention provides a method for treating a condition in a mammal characterized by undesired thrombosis comprising administering to said mammal a therapeutically effective amount of:

(1) [2-({4-[(dimethylamino)iminomethyl]phenyl}carbonylamino)-5-methoxyphenyl]-N-(5-chloro(2-pyridyl))carboxamide, or a pharmaceutically acceptable salt thereof; and (2) an anticoagulant agent.

In some embodiments of the second group, the anticoagulant agent is selected from the group consisting of specific inhibitors of thrombin, factor IXa, factor XIa, factor XIIa or factor VIIa, synthetic pentasaccharides, low molecular weight heparin, anti-tissue factor antibody and combinations thereof.

In some embodiments of the second group, the anticoagulant agent is an injectable anticoagulant agent.

In some embodiments of the second group, the anticoagulant agent is selected from the group consisting of bivalirudin, dabigatran, argatroban, lepirudin, warfarin, and phenocoumarol.

In some embodiments of the second group, the anticoagulant agent is selected from the group consisting of fondaparinux, danaparoid, enoxaparin, dalteparin and unfractionated heparin.

In some embodiments of the second group, the anticoagulant agent is enoxaparin.

In a third group of embodiments, the invention provides a method for treating a condition in a mammal characterized by undesired inflammation or undesired thrombosis comprising administering to said mammal a therapeutically effective amount of:

(1) [2-({4-[(dimethylamino)iminomethyl]phenyl}carbonylamino)-5-methoxyphenyl]-N-(5-chloro(2-pyridyl))carboxamide, or a pharmaceutically acceptable salt thereof; and (2) an anti-inflammatory agent.

In some embodiments of the third group, the anti-inflammatory agent is selected from the group consisting of non-steroidal anti-inflammatory agents, tumor necrosis factor antagonists, interleukin 1 receptor antagonists, cyclooxygenase-2 inhibitors and rheumatoid arthritis agents.

In some embodiment of the third group, the anti-inflammatory agent is selected from the group consisting of acetylsalicylic acid, piroxicam, indomethacin, mesalamine, sulfasalazine, methotrexate, leflunomide, etanercept, infliximab, adalimubab, and anakinra.

In some embodiment of the third group, the anti-inflammatory agent is acetylsalicylic acid.

In a fourth group of embodiments, the invention provides a method for treating a condition in a mammal characterized by undesired thrombosis comprising administering to said mammal a therapeutically effective amount of:

(1) [2-({4-[(dimethylamino)iminomethyl]phenyl}carbonylamino)-5-methoxyphenyl]-N-(5-chloro(2-pyridyl))carboxamide, or a pharmaceutically acceptable salt thereof; and (2) a blood pressure lowering agent.

In some embodiments of the fourth group, the blood pressure lowering agent is selected from the group consisting of diuretics, beta blockers, angiotensin converting enzyme inhibitors, angiotensin 2 receptor antagonists, and calcium channel blockers.

In some embodiments of the fourth group, the blood pressure lowering agent is verapamil.

In some other embodiments of the fourth group, the blood pressure lowering agent is diltiazem.

In some embodiments of the fourth group, the blood pressure lowering agent is amiodarone.

In some embodiments of the fourth group, the blood pressure lowering agent is metoprolol.

In some embodiments of the fourth group, the blood pressure lowering agent is carvedilol.

In some embodiments of the above first to fourth groups of embodiments, at least one of the therapeutic agents is administered in a sub-therapeutic dosage.

In some embodiments of the above first to fourth groups of embodiments, both of the therapeutic agents are administered in sub-therapeutic dosages.

In some embodiments of the above first to fourth groups of embodiments, the two therapeutic agents are administered simultaneously.

In some embodiments of the above first to fourth groups of embodiments, the two therapeutic agents are administered sequentially.

In some embodiments of the above first to fourth groups of embodiments, the pharmaceutically acceptable salt of [2-({4-[(dimethylamino)iminomethyl]phenyl}carbonylamino)-5-methoxyphenyl]-N-(5-chloro(2-pyridyl))carboxamide is the maleate salt.

In some embodiments of the first to fourth groups of embodiments, the method further comprises administering to said mammal a therapeutically effective amount of:

(3) a therapeutic agent selected from other antiplatelet agents, anticoagulant agents, thrombin inhibitors, thrombolytic agents, anti-arrhythmic agents, blood pressure lowering agents, cholesterol, and triglyceride lowering agents.

In some embodiments of the above first to fourth groups of embodiments, the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

The invention is also directed to pharmaceutical compositions comprising a compound of the following formula:

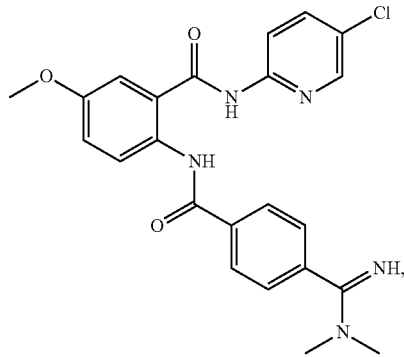

which has the chemical name, [2-({4-[(dimethylamino)iminomethyl]phenyl}carbonylamino)-5-methoxyphenyl]-N-(5-chloro(2-pyridyl))carboxamide and another therapeutic agent, including, an antiplatelet agent, an anticoagulant agent, an inflammatory agent, and combinations thereof.

In a fifth group of embodiments, the invention provides a pharmaceutical composition comprising:

(1) [2-({4-[(dimethylamino)iminomethyl]phenyl}carbonylamino)-5-methoxyphenyl]-N-(5-chloro(2-pyridyl))carboxamide, or a pharmaceutically acceptable salt thereof;

(2) an antiplatelet agent;

and a pharmaceutically acceptable carrier.

In some embodiments of the fifth group, the antiplatelet agent is a GP IIb/IIIa receptor antagonist.

In some embodiments of the fifth group, the antiplatelet agent is a P2Y$_{12}$ receptor antagonist.

In some embodiments of the fifth group, the antiplatelet agent is a phosphodiesterase III inhibitor.

In some embodiments of the fifth group, the antiplatelet agent is a thromboxane synthase inhibitor.

In some embodiments of the fifth group, the antiplatelet agent is a thromboxane A2 receptor antagonist.

In some embodiments of the fifth group, the antiplatelet agent is a thrombin receptor antagonist.

In still some embodiments of the fifth group, the antiplatelet agent is an inhibitor of p selectin.

In some embodiments of the fifth group, the antiplatelet agent is selected from the group consisting of: abciximab, eptifibatide, tirofiban, acetylsalicylic acid, cangrelor, ticagrelor, clopidogrel, ticlopidine, prasugrel, dipyridamole, aggrenox, SCH530348, ifetroban, cilostazol, isbogrel, furegrelate, ramatroban, ridogrel, terbogrel, Servier S 18886 and ozagrel.

In some embodiments of the fifth group, the antiplatelet agent is eptifibatide.

In some embodiments of the fifth group, the antiplatelet agent is clopidogrel.

In a sixth group of embodiments, the invention provides a pharmaceutical composition comprising:
(1) [2-({4-[(dimethylamino)iminomethyl]phenyl}carbonylamino)-5-methoxyphenyl]-N-(5-chloro(2-pyridyl))carboxamide, or a pharmaceutically acceptable salt thereof;
(2) an anticoagulant agent;
and a pharmaceutically acceptable carrier.

In some embodiments of the sixth group, the anticoagulant agent is selected from the group consisting of specific inhibitors of thrombin, factor IXa, factor Xa, factor XIIa, factor XIa or factor VIIa, synthetic pentasaccharide, low molecular weight heparin, anti tissue factor antibodies and combinations thereof.

In some embodiments of the sixth group, the anticoagulant agent is an injectable anticoagulant agent.

In some embodiments of the sixth group, the anticoagulant agent is selected from the group consisting of bivalirudin, dabigatran, argatroban, lepirudin, warfarin, and phenocoumarol.

In some embodiments of the sixth group, the anticoagulant agent is selected from the group consisting of fondaparinux, danaparoid, enoxaparin, dalteparin and unfractionated heparin.

In some embodiments of the sixth group, the anticoagulant agent is enoxaparin.

In a seventh group of embodiments, the invention provides a pharmaceutical composition comprising:
(1) [2-({4-[(dimethylamino)iminomethyl]phenyl}carbonylamino)-5-methoxyphenyl]-N-(5-chloro(2-pyridyl))carboxamide, or a pharmaceutically acceptable salt thereof;
(2) an anti-inflammatory agent;
and a pharmaceutically acceptable carrier.

In some embodiments of the seventh group, the anti-inflammatory agent is selected from the group consisting of non-steroidal anti-inflammatory agents, tumor necrosis factor antagonists, interleukin 1 receptor antagonists, cyclooxygenase-2 inhibitors and rheumatoid arthritis agents.

In some embodiments of the seventh group, the anti-inflammatory agent is selected from the group consisting of acetylsalicylic acid, piroxicam, indomethacin, mesalamine, sulfasalazine, methotrexate, leflunomide, etanercept, infliximab, adalimubab, and anakinra.

In some embodiments of the seventh group, the anti-inflammatory agent is acetylsalicylic acid.

In an eighth group of embodiments, the invention provides a pharmaceutical composition comprising:
(1) [2-({4-[(dimethylamino)iminomethyl]phenyl}carbonylamino)-5-methoxyphenyl]-N-(5-chloro(2-pyridyl))carboxamide, or a pharmaceutically acceptable salt thereof;
(2) a blood pressure lowering agent;
and a pharmaceutically acceptable carrier.

In some embodiments of the eighth group, the blood pressure lowering agent is selected from the group consisting of diuretics, beta blockers, angiotensin converting enzyme inhibitors, angiotensin 2 receptor antagonists and calcium channel blockers.

In some embodiments of the eighth group, the blood pressure lowering agent is verapamil.

In some embodiments of the eighth group, the blood pressure lowering agent is diltiazem.

In some embodiments of the eighth group, the blood pressure lowering agent is amiodarone.

In some embodiments of the eighth group, the blood pressure lowering agent is metoprolol.

In some embodiments of the eighth group, the blood pressure lowering agent is carvedilol.

In some embodiments of the fifth to eighth groups of embodiments, at least one of the therapeutic agents is present in a sub-therapeutic dosage.

In some embodiments of the fifth to eighth groups of embodiments, both of the therapeutic agents are present in sub-therapeutic dosages.

In some embodiments of the fifth to eighth groups of embodiments, the pharmaceutically acceptable salt of [2-({4-[(dimethylamino)iminomethyl]phenyl}carbonylamino)-5-methoxyphenyl]-N-(5-chloro(2-pyridyl))carboxamide is the maleate salt.

In some embodiments of the fifth to eighth groups of embodiments, the composition further comprises:
(3) a therapeutic agent selected from other antiplatelet agents, other anti-coagulants, thrombin inhibitors, thrombolytic agents, anti-arrhythmic agents, blood pressure lowering agents, cholesterol or triglyceride lowering agents.

In a ninth group of embodiments, the invention provides a kit comprising:
(1) a first container, wherein said container contains [2-({4-[(dimethylamino)iminomethyl]phenyl}carbonylamino)-5-methoxyphenyl]-N-(5-chloro(2-pyridyl))carboxamide, or a pharmaceutically acceptable salt thereof; and
(2) a second container, wherein said container contains another therapeutic agent selected from the group consisting of antiplatelet agents, anticoagulant agents, and anti-inflammatory agents.

In some embodiments of the ninth group of embodiments, the invention provides a kit further comprising:
(3) a package insert stating that the two therapeutic agents can be used together.

In some embodiments of the ninth group, the pharmaceutically acceptable salt of [2-({4-[(dimethylamino)iminomethyl]phenyl}carbonylamino)-5-methoxyphenyl]-N-(5-chloro(2-pyridyl))carboxamide is the maleate salt.

In some embodiments of the ninth group, at least one of the therapeutic agents is present in a sub-therapeutic dosage.

In some embodiments of the ninth group, both of the therapeutic agents are present in sub-therapeutic dosages.

III. COMBINATION THERAPY

The present invention provides methods of treating a condition in a mammal characterized by undesired thrombosis using a combination of Compound A with another therapeutic agent.

A combination of Compound A with an antiplatelet agent, eptifibatide, at concentrations which individually do not produce significant inhibition of thrombosis under the experimental conditions, has been shown to have substantially enhanced antithrombotic activity in flow based assay systems (Example 4). Animal experiments in rats showed a more than additive antithrombotic activity when a combination of Compound A and an antiplatelet agent, such as clopidogrel or aspirin, at sub-therapeutic doses was used (see Example 5 and Examples 11 and 12).

Example 5 shows the synergism between Compound A and clopidogrel, an antagonist of the platelet $P2Y_{12}$ receptor in inhibition of rat arterial thrombosis. Example 13 corroborates the antithrombotic effect of factor Xa and $P2Y_{12}$ dual inhibition by showing that a significantly lower plasma concentration of Compound A was able to produce a significant delay in thrombosis formation and occlusion times in mice with deficient $P2Y_{12}$ expression on platelet as compared to the plasma concentration of Compound A needed to produce similar levels of delay in wild-type mice.

It is also contemplated that a combination of Compound A and an injectable anticoagulant agent will provide superior safety profile for a given level of anticoagulation, leading to improved clinical results. Existing data show that a combination of an antiplatelet agent with an anticoagulant agent (e.g. combination of a GP IIb/IIIa antagonist with unfractionated heparin or a GP IIb/IIIa antagonist with specific thrombin inhibitor bivalirudin) leads to unacceptable levels of bleeding in treated patients. (Stone, G W, et al, Bivalirudin in Patients with Acute Coronary Syndromes Undergoing Percutaneous Coronary Intervention: A Subgroup Analysis from the Acute Catheterization and Urgent Intervention Triage Strategy (ACUITY) Trial, *Lancet*, 2007, 369(9565):907-19.) A dose ranging trial of the low molecular weight heparin enoxaparin in patients with myocardial infarction compared 1 mg/kg and 1.25 mg/kg doses of the anticoagulant. Even a small change in dosing (25% increase) led to unacceptable levels of major hemorrhage (Dose-ranging Trial of Enoxaparin for Unstable Angina: Results of TIMI 11A. The Thrombolysis in Myocardial Infarction (TIMI) 11A Trial Investigators, *J. Am. Coll. Cardiol.*, 1997, 29(7):1474-82) and the 1.25 mg/kg dose was not studied any further.

In contrast, Compound A has been shown to have a wider dose range (80 mg and 30 mg/day) in a Phase II trial. In a randomized clinical trial of 215 orthopedic surgery patients undergoing knee replacement, Compound A at doses of 30 mg and 80 mg/day was effective in preventing venous thromboembolic events such as symptomatic or asymptomatic deep vein thrombosis and pulmonary embolism. More on the effective unit dose of Compound A can be found in PCT/US2007/084887 filed Nov. 15, 2007, entitled "Unit Dose Formulation and Methods of Treating Thrombosis with an Oral Factor Xa Inhibitor". The level of antithrombotic efficacy was comparable to that attained by the low molecular weight heparin enoxaparin (Example 6) (Turpie, A G, et al, Abstract # P-T-652, XXIst Congress of the International Society of Thrombosis and Haemostasis, Geneva, July, 2007). In addition, data from the trial show a wider safety margin than is available with current anticoagulant agents. Recent data evaluating bleeding time in monkeys show that therapeutic levels of Compound A (plasma concentrations between 5 to 25 ng/mL) did not cause extension of bleeding (see Example 7). Thus, it is contemplated that the novel combination of Compound A with an existing antiplatelet agent inhibits thrombus formation with a wider safety margin. Further, in situations where bridging therapy is necessary for a patient receiving parenteral anticoagulant agent to switch to an oral anticoagulant agent for chronic dosing, Compound A is considered a potential bridging oral anticoagulant agent to be used in combination with low molecular weight heparin or pentasaccharide.

It is further contemplated that a combination of Compound A and a standard anti-inflammatory agent provides superior efficacy profile for reduction in levels of circulating cytokines, which can lead to improved therapeutic responses in diseases such as atherosclerosis which are known to be mediated by inflammatory stimuli. Oral anticoagulants such as warfarin are not capable of reduction of circulating markers of inflammation and achieving systemic effects in the vasculature.

It has been reported that Factor Xa has an enhancing effect on the inflammatory activity of cytokine mediated signaling (PNAS). (Hezi-Yamit, A. et al, Synergistic Induction of Tissue Factor by Coagulation Factor Xa and TNF: Evidence for Involvement of Negative Regulatory Signaling Cascades, *Proc. Nat'l. Acad. Sci. USA*, 2005 102(34):12077-82). Enzymes of the blood coagulation pathway enhance the inflammatory response leading to endothelial dysfunction, accounting, in part, for the vascular complications occurring in sepsis and cardiovascular diseases. The responses of endothelial cell activation include, induction of the expression of tissue factor, a membrane glycoprotein that promotes thrombosis, and of E-selectin, a cell adhesion molecule that promotes inflammation. It was demonstrated that synergistic interactions between factor Xa and the pro-inflammatory cytokines, tumor necrosis factor, interleukin 1 or CD40L, enhanced expression of tissue factor and E-selectin in endothelial cells (PNAS). These synergistic interactions led to amplification of cytokine-induced inflammatory activity such as activation of endothelial cells.

However, Compound A, a factor Xa inhibitor, did not exhibit a statistically significant effect on the reduction of the amount of cytokine released from blood cells in an ex vivo human whole blood system when used alone. Surprisingly, when Compound A was added to blood from aspirinated donors, it provided additional suppression of cytokine release over that provided by aspirin alone in a dose responsive manner (see Example 9). This shows that a combination of Compound A with anti-inflammatory agents has the potential of achieving additional anti-inflammatory therapeutic benefit since cytokines are among the principal mediators of inflammation.

It is further contemplated that in patients being treated for atrial fibrillation, blood pressure lowering drugs such as beta blockers or calcium channel blockers and Compound A may be used concomitantly. Drugs like verapamil are known inhibitors of p-glycoprotein function. Compound A has been identified to be a substrate of p-glycoprotein in in vitro evaluations. As expected, experimental results of the present invention in telemeterized dogs using a combination of Compound A and verapamil show that the plasma concentrations of Compound A in dogs with dual treatment were about two times higher than those on single treatment. However, Compound A did not change the measures of blood pressure upon coadministration with verapamil, providing evidence that Compound A may be safely used with a blood pressure reducing agent such as verapamil. See Example 10.

Accordingly, it is contemplated that the method of treatment using a combination of Compound A and another therapeutic agent will not produce undesired drug-drug interaction or other additional side effects over the agents alone. It is further contemplated that the combination can offer an efficacy or safety advantage over the agents alone and/or produces a synergic effect. Synergism can be in terms of increased antithrombotic efficacy, improved safety profile, or other beneficial effect of the combination as compared with the individual agent. It occurs when the therapeutic effect of the compounds when administered in combination is greater than the additive effect of the compounds when administered alone as a single agent. In such a case, the therapeutically effective amount of the agents in the combination therapy may be lower than the effective or optimal amount needed when the agents are used alone. It is contemplated that lower dosages will minimize potential side effects of an agent, thus lead to improved safety profile. Thus, the combination preferably allows one of the therapeutic agents to be used at a sub-therapeutic dosage. In one embodiment, the combination allows both therapeutic agents to be used at sub-therapeutic dosages.

Compound A and the other therapeutic agent may be formulated into two separate pharmaceutical compositions. They may be administered at the same time or sequentially in any order. Preferably, when administered sequentially, the two agents are administered sufficiently closely in time so that the desired therapeutic effect can be provided. Compound A and the other therapeutic agent may also be formulated into a single pharmaceutical composition. Compound A and two other therapeutic agents may also be administered at the same time or sequentially in any order. Preferably, when administered sequentially, the three agents are administered sufficiently closely in time so that the desired therapeutic effect can be provided. They may also be formulated into a single pharmaceutical composition or any two of them may be formulated into a single pharmaceutical composition.

IV. COMPOSITION AND DOSAGE

The present invention further provides a novel composition comprising Compound A or a pharmaceutically acceptable salt thereof, another therapeutic agent, and a pharmaceutically acceptable carrier.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical compositions may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The compositions of this invention are formulated for pharmaceutical administration to a mammal, preferably a human being. Such pharmaceutical compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, long-acting, sustained-releasing. Still further, compounds can be administered in a local rather than systemic means, such as administration (e.g., injection) as a sustained release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be in any orally acceptable dosage form, including capsules, tablets, aqueous suspensions or solutions. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative, such as benzylalkonium chloride. Alternatively, for ophthalmic uses, the pharmaceutical compositions may be formulated in an ointment, such as petrolatum.

The pharmaceutical compositions of this invention may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

Any of the above dosage forms containing effective amounts are within the bounds of routine experimentation and within the scope of the invention. A therapeutically effective dose may vary depending upon the route of administration and dosage form. The preferred combination of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. Combination therapies of this invention may be administered in a single daily dose, or may be administered two, three, or four times daily.

Typically, about 0.5 to 500 mg of Compound A or a salt or mixture of salts of Compound A is compounded with a physiologically acceptable vehicle, carrier, excipient, binder, preservative, stabilizer, dye, flavor etc., as called for by accepted pharmaceutical practice. When Compound A and the co-administrating agent are formulated into a single pharmaceutical composition, about 0.5 to 500 mg of the co-administering agent is added to the above composition. The amount of the active ingredient(s) in these compositions is such that a suitable dosage in the range indicated below is obtained.

It is contemplated that a typical dosage of Compound A in the combination therapies will range from about 0.001 mg/kg to about 1000 mg/kg, preferably from about 0.01 mg/kg to about 2.0 mg/kg, and more preferably from about 0.1 mg/kg to about 1.5 mg/kg, and even more preferably from about 0.4 mg/kg to about 1.2 mg/kg. Still more preferably, the dosage of Compound A in the combinations is lower than 0.5 mg/kg.

The dosages of the other therapeutic agents when used alone are known to or can be obtained by those skilled in the art. It is contemplated that the dosages of these agents when used in combination with Compound A will not exceed the maximum dosages of the individual agents. Preferably, the dosages in the combination therapies are less than the maximum dosages and more preferably, the dosages in the combination therapies are sub-therapeutic dosages. It is contemplated that the dosages of Compound A or the other therapeutic agents may be adjusted to reflect the synergism of the combination therapies, which can be determined by one skilled in the art based on the information provided herein.

In addition to dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed in the combination, the age, body weight, general health, sex and diet, renal and hepatic function of the patient, and the time of administration, rate of excretion, combination with other drugs, judgment of the treating physician or veterinarian and severity of the particular disease being treated. The amount of active ingredients will also depend upon the therapeutic agent combined with Compound A.

V. KIT OF PARTS

The invention further provides a novel kit or package. The kit of the present invention comprises: (a) a first container containing Compound A or pharmaceutically acceptable salt forms thereof; and (b) a second container containing another therapeutic agent. In some embodiments, the kit further contains (c) a package insert stating that the two pharmaceutical agents can be used together for the treatment of a condition characterized by undesired thrombosis. In some other embodiment, the kit also comprises a third container containing a third therapeutic agent and may further comprise a package insert stating that the three pharmaceutical agents can be used in combination to treat a condition characterized by undesired thrombosis.

The first, second and/or third container may be a bottle, jar, vial, flask, syringe, tube, bag, or any other container used in the manufacture, storage, or distribution of a pharmaceutical product. The package insert can be a label, tag, marker, or the like, that recites information relating to the pharmaceutical composition of the kit. The information recited will usually be determined by the regulatory agency governing the area in which the pharmaceutical composition is to be sold, such as the United States Food and Drug Administration. Preferably, the package insert specifically recites the indications for which the pharmaceutical composition has been approved. The package insert may be made of any material on which a person can read information contained therein or thereon. Preferably, the package insert is a printable material, such as paper, adhesive-backed paper, cardboard, foil, or plastic, and the like, on which the desired information has been printed or applied.

VI. EXAMPLES

Unless stated otherwise, the abbreviations used throughout the specification have the following meanings:

| | |
|---|---|
| ACN = | acetonitrile |
| aq. = | aqueous |
| Arg = | arginine |
| ASA = | aspirin |
| bid = | twice daily |
| CI = | Confidence Interval |
| cm = | centimeter |
| DCM = | dichloromethane |
| EDTA = | ethylenediaminetetraacetic acid |
| EGTA = | ethylene glycol tetraacetic acid |
| eq. = | equivalent |
| EtOH = | ethanol |
| g = | gram |
| Gly = | glycine |
| HexLi = | hexyl lithium |
| $HNMe_2$ = | Dimethylamine |
| HPLC = | high performance liquid chromatography |
| HPLC = | high performance liquid chromatography |
| hr = | hour |
| kg = | kilogram |
| L = | liter |
| LOD = | limit of detection |
| M = | molar |

| | |
|---|---|
| Me = | methyl |
| MeO = | methoxy |
| MeOH = | methanol |
| mg = | milligram |
| min = | Minute(s) |
| mL = | milliliter |
| mm = | millimeter |
| mmHg*min = | (Millimeter Mercury) × (min) |
| N = | normal |
| nM = | nanomolar |
| nm = | nanometer |
| NMR = | nuclear magnetic resonance |
| pg = | picogram |
| Pro = | proline |
| rpm = | revolutions per minute |
| $s^{-1}$ = | per second |
| Std.= | standard |
| THF = | tetrahydrofuran |
| THF = | tetrahydrofuran |
| U = | unit |
| μG = | microgram |
| μM = | micromolar |

Example 1

Preparation of Compound A

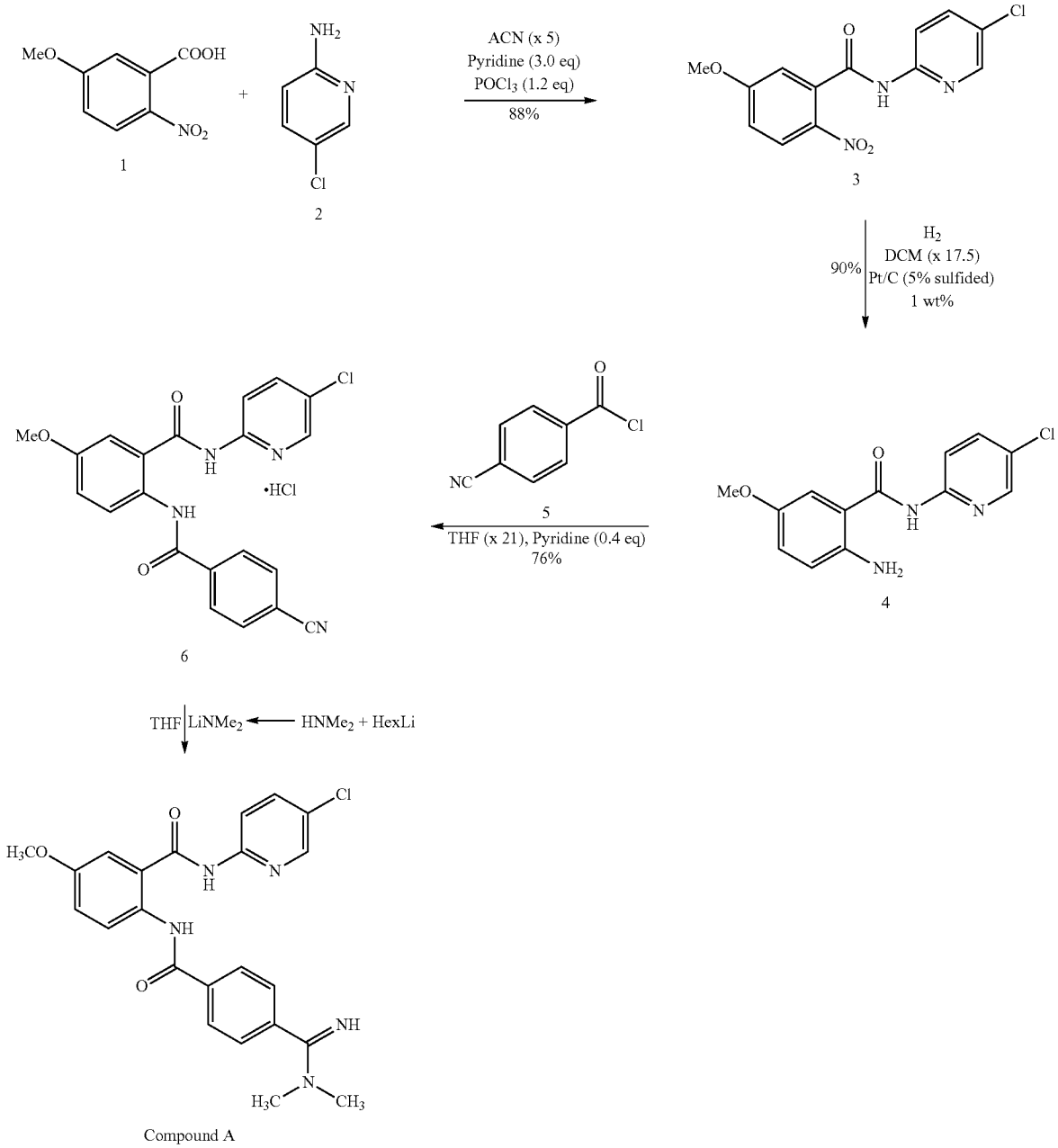

Compound A

Step 1:

5-Methoxy-2-nitrobenzoic acid (1) (25.0 kg, 1.0 eq), 2-amino-5-chloropyridine (2) (16.3 kg, 1.0 eq), and acetonitrile (87.5 kg, 3.5 parts) were charged to a 380 L GLMS reactor. The reaction mixture was adjusted to 22° C. (19 to 25° C.) and anhydrous pyridine (30.0 kg, 3.0 eq) was added. The pump and lines were rinsed forward with acetonitrile (22.5 kg, 0.9 parts), and the reactor contents were adjusted to a temperature of 19-22° C. Phosphorous oxychloride (23.3 kg, 1.20 eq) was charged to the contents of the reactor via a metering pump, while maintaining a temperature of 25° C. (22-28° C.). The metering pump and lines were rinsed forward with acetonitrile (12.5 kg, 0.5 parts), while keeping the temperature at 25° C. (22-28° C.). The reaction mixture normally turned from a slurry to a clear solution after the addition of about ⅓ of the POCl$_3$. At the end of the addition, it became turbid. After complete addition, the reaction mixture was agitated at 25° C. (22-28° C.) for ca. 1 hr, at which time HPLC analysis confirmed reaction completion. The solution was cooled to 15° C. (12-18° C.) and drinking water (156.3 kg, 6.25 parts) was charged slowly while keeping reaction temperature between 12 and 30° C. The reaction mixture was then adjusted to 22° C. (19 to 25° C.) and agitated for ca. 5 hrs until exotherm ceased. Formation of a slurry was visually confirmed and the contents of the reactor were filtered onto a pressure nutsche fitted with filter cloth. The reactor, pump, and lines were washed forward onto the pressure nutsche with two portions of drinking water (62.5 kg, 2.5 parts each). The filtrate had a pH value of 7. The product (41.8 kg) was dried under vacuum with a maximum temperature of water bath (to heat dryer jacket) of 50° C. After ca. 12 hrs, in-process LOD analysis indicated a solvent content of 0.72%. The dry product (3) was discharged (34.4 kg) with 88.2% yield and 99.1% purity by HPLC.

Step 2:

To a 780 L Hastelloy reactor, compound 3 (33 kg, 1.0 eq), 5% platinum carbon (sulfided, 0.33 kg, 0.010 parts) and dichloromethane (578 kg, 17.5 parts) were charged. Agitation was started and reactor contents were adjusted to 22° C. (19 to 25° C.). The reactor was pressurized with ca. 30 psi hydrogen and the reaction mixture gently heated to 28° C. (25-31° C.). Hydrogenation of the reactor contents was performed under ca. 30 psi at 28° C. (25 to 31° C.; maximum 31° C.) until the reaction was complete by HPLC. After 16.5 hrs, the reaction was deemed complete after confirming the disappearance of starting material (0.472%). The contents of the reactor were circulated through a conditioned celite pad (0.2-0.5 kg celite conditioned with 20-55 kg dichloromethane) prepared in an 8" sparkler filter to remove the platinum catalyst. The reactor and celite bed were rinsed forward with two portions of dichloromethane (83 kg, 2.5 parts each). The filtrate was transferred to and concentrated in a 570 L GLMS reactor under an atmospheric pressure to ca. 132 L (4 parts volume). Ethanol (69 kg, 2.1 parts) was charged and concentration continued under atmospheric pressure to ca. 99 L (3 parts volume). In-process NMR indicated that the dichloromethane content was 39%. Ethanol (69 kg, 2.1 parts) was charged again and concentration continued again to ca. 99 L (3 parts volume). In-process NMR indicated that the dichloromethane content was 5%. The reaction mixture was then adjusted to 3° C. (0 to 6° C.), agitated for ca. 1 hr, and the resulting slurry filtered onto a jacketed pressure nutsche fitted with filter cloth. The reactor, pump, and lines were rinsed forward with cold (3° C. (0-6° C.)) ethanol (26 kg, 0.8 parts). The wet filter cake (36.6 kg) was dried under vacuum at 40-50° C. with a maximum temperature of water bath (to heat dryer jacket) of 50° C. LOD analysis after 12.5 hrs indicated solvent content was at 0.1%. The dry product (4) was discharged (26.4 kg) in 89.5% yield. HPLC showed 98.4% purity, with dechlorinated impurity at 0.083%.

Step 3:

To a 780 L Hastelloy reactor, was charged 4-cyanobenzoyl chloride (5) (17.2 kg, 1.1 eq) and THF (92 kg, 3.5 parts). Reactor contents were agitated at 22° C. (19 to 25° C.) until all of the solids had dissolved. The resulting solution was transferred to a lower receiver and the reactor was rinsed forward with THF (26 kg, 1 part). Compound 4 (26.4 kg, 1 eq), THF (396 kg, 15 parts) and pyridine (2.90 kg, 0.4 eq) were charged to a clean reactor. The pump and lines were rinsed forward with THF (34 kg, 1.3 parts). Via a metering pump, the 4-cyanobenzoyl chloride/THF solution was charged to the reactor, keeping the temperature at ≦30° C. and rinsing forward with THF (ca. 10 kg). The resulting yellow-colored slurry was agitated at 22° C. (19 to 25° C.) for ca 2 hrs. In-process HPLC taken after 2 hrs showed a compound 4 content of 0%, indicating completion of the reaction. The slurry was filtered onto a pressure nutsche fitted with filter cloth. The reactor, pump, lines, and wet cake were rinsed with three portions of ethanol (ca. 15 kg each). The wet filter cake was discharged (65.4 kg) and transferred back to the reactor for slurry wash in ethanol (317 kg, 12 parts) at 22° C. (19 to 25° C.) for ca. 1 hr. The slurry was filtered onto the pressure nutsche and the reactor, pump, lines, and wet filter cake were rinsed with two portions of ethanol (ca. 15 kg each) and two portions of THF (ca. 15 kg each). The wet filter cake was dried under vacuum with a maximum temperature of warm glycol bath (to heat the reactor jacket) of 40° C. After 14.5 hrs of drying, LOD was 0.75%. The dried material was milled (screen 0.125") to give 31.8 kg of compound 6, which was dried under vacuum for another 10.5 hrs. LOD after drying was 1.8%, and the product was discharged (31.5 kg) in 74.8% yield (expected 60-90%). HPLC showed 100% purity.

Step 4:

A slurry of compound 6 (455 g, 1.0 eq.) in THF (4.67 kg, 10.3 parts) was prepared and adjusted to <10° C. Lithium dimethyl amide was prepared as follows: hexyllithium (2.3 N/hexane, 2.45 L, 5.5 eq.) was added to dimethylamine solution (2 N/THF, 2.8 L, 5.5 eq.) maintaining <10° C. The lithium dimethyl amide solution was charged into the slurry containing the compound 6 keeping the pot temperature of <10° C. The reaction progress was monitored by in-process HPLC which confirmed that the amount of compound 6 was <1.0%. A buffer solution of NaHCO$_3$ (490 g, 1.1 parts, 5.7 eq.) and Na$_2$CO$_3$ (490 g, 1.1 parts, 4.5 eq.) in deionized water (6.6 kg, 14.51 parts) was prepared, and above reaction mixture was transferred to this aqueous solution maintaining <5° C. The product precipitated out and the resulting slurry was adjusted to 20° C. over a period of 12 hr. The solid was filtered, and the resulting wet cake was washed with 3.5 kg (7.7 parts) of deionized water. The solid was filtered off using a coarse frit glass bench filter, and rinsed forwarded with cold (0-5° C.) absolute ethanol (628 g, 1.4 parts). The product Compound A was dried at 30-35° C. Dry product was obtained in 458 g (73% yield).

Example 2

Thrombin Generation Inhibition Assay

In this method, human plasma samples containing the peptide gly-pro-arg-pro (SEQ ID NO: 1) (Pefabloc FG, Centerchem) as an anticlotting agent, were treated with tissue factor (Innovin, Dade Behring) to initiate the generation of thrombin. After 10 min, the reaction was stopped by addition of EGTA. A chromogenic peptide substrate (Spectrozyme TH, American Diagnostica) specific for thrombin was added to measure the activity of thrombin generated during the tissue factor treatment period. After allowing the substrate cleavage reaction to proceed for 2 min, the samples were quenched with glacial acetic acid. The plasma samples were analyzed in triplicate in a 96-well plate format. Control samples containing pooled platelet poor plasma with or without added Compound A were assayed in quadruplicate on each plate. The control samples were used to establish plate acceptance criteria. Absorbance of each sample well was measured at 405 nm.

Thrombin generation (% Inhibition) was calculated from absorbance at 405 nm (A405) by the following equation:

%Inhibition=(1−$A$405/Baseline)×100.

The Baseline in the equation was the mean absorbance at 405 nm produced by pooled plasma in the absence of Compound A. The coefficient of variation (CV) for both control and clinical samples was 20%. Since thrombin generation inhibition values were reported as a percentage there is no lower limit of quantitation in this assay.

Figure 2:
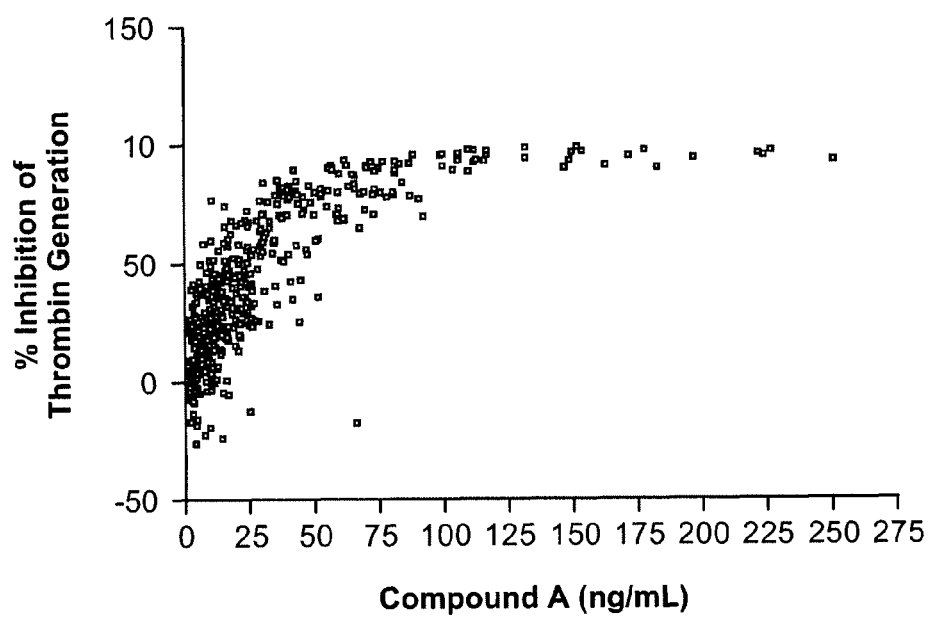

FIG. 1 shows the % inhibition of thrombin generation produced by human plasma samples from healthy volunteers who were administered single ascending doses of Compound A. FIG. 2 shows the % inhibition of thrombin generation produced by human plasma samples from healthy volunteers who were administered multiple ascending doses of Compound A. These Figures show a good correlation between Compound A plasma concentration and inhibition of thrombin generation.

Example 3

Anti-Factor Xa Unit Assay

The anti-factor Xa (anti-fXa) assay was adapted from a commercial kit (Diapharma COATEST LMW Heparin) and modified to a 96-well format. A low molecular weight heparin, dalteparin, included in the kit was used to construct a standard curve according to the manufacture's instruction using pooled platelets poor plasma. All samples and standards were assayed in duplicate. The limit of quantitation was 0.05 U/mL and results below 0.05 U/mL were reported as below the limit of quantitation. The upper limit of measurement for the plate assay was 1.0 U/mL and samples with anti-factor Xa units higher than 1.0 U/mL were re-assayed after dilution. The coefficient of variation (CV) for both standards and clinical samples were 10%.

Figure 3:
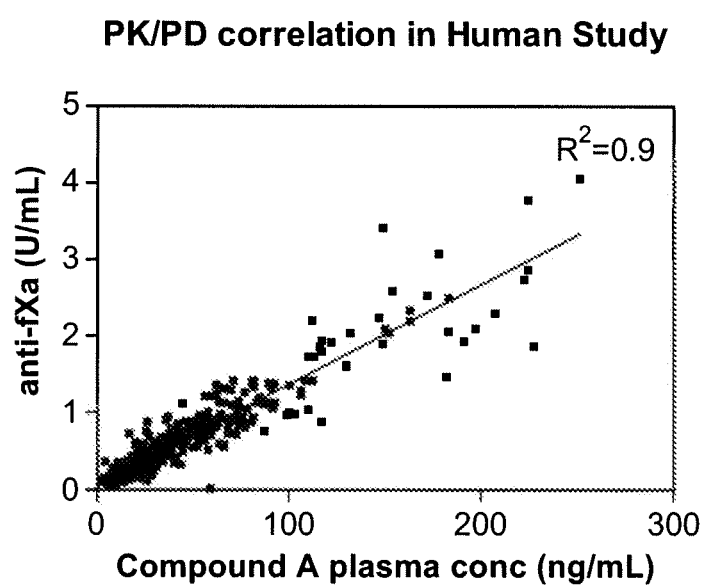
FIG. 3 shows the correlation of Compound A plasma concentration and anti-factor Xa units in a human study.

FIG. 3 shows the anti-factor Xa units generated by plasma samples from healthy volunteers who were administered multiple ascending doses of Compound A.

Example 4

Combination of Compound A and Eptifibatide, a GP IIb/IIIa Antagonist

Experiments in the real time perfusion chamber were carried out in order to measure if anticoagulation of blood by Compound A was capable of providing additional antithrombotic activity over that attained by therapeutic doses of the antiplatelet agent eptifibatide, a GP IIb/IIIa antagonist. Capillaries were coated with a mixture of collagen and tissue factor and human whole blood containing fluorescently labeled fibrinogen (Alexa 546 labeled fibrinogen) was perfused over the coated surface at a shear rate of 300 s$^{-1}$. After the perfusion, the thrombotic activity was quantified by measurement of labeled fibrin produced as a result of fibrinogen cleavage during the activation of platelets and the blood coagulation system. For this series of experiments in five healthy human volunteers, blood was obtained by venipuncture and treated with 2.4 μM eptifibatide. The dose of eptifibatide corresponds to the plasma concentration attained by therapeutic concentrations of the GPIIb/IIIa inhibitor.

Table 1 shows the dose responsive inhibition of thrombosis by Compound A and eptifibatide, a platelet GP IIb/IIIa receptor antagonist, upon perfusion of whole human blood over a collagen and tissue factor coated surface. Quantitation of fluorescently labeled fibrinogen/fibrin is shown for five blood donors.

As shown in Table 1, a therapeutic concentration of the antiplatelet agent is not sufficient to inhibit thrombosis under the assay conditions. However, ex vivo addition of the factor Xa inhibitor Compound A provides additional antithrombotic activity in a dose responsive manner. Thus administration of Compound A as a concomitant medication during the use of antiplatelet agents is likely to provide additional benefits of antithrombotic efficacy.

TABLE 1

| Compound A Concentration (nM) | Mean Fluorescence | Standard Deviation |
| --- | --- | --- |
| 0 | 118.0 | 40.4 |
| 10 | 107.7 | 51.4 |
| 25 | 85.0 | 48.4 |
| 50 | 64.5 | 39.5 |
| 75 | 34.7 | 22.91 |
| 100 | 33.0 | 34.7 |

Example 5

Combination of Compound A and Clopidogrel, a P2Y$_{12}$ Receptor Antagonist

The combination effect of antiplatelet and anticoagulant was investigated in an in vivo model of thrombosis using a specific antagonist of P2Y$_{12}$ receptor, clopidogrel, which has been shown to be capable of inhibiting ADP induced platelet aggregation of both human and rat platelets. This well characterized animal model (Lockyer and Kambayashi, Demonstration of Flow and Platelet Dependency in a Ferric Chloride Induced Model of Thrombosis, *J. Cardiovasc. Pharmacol.* 1999, 33(5):718-25) has been previously used to test both anticoagulants and antiplatelet agents. In this experiment, the ability of Compound A to maintain vessel patency under arterial flow conditions in ferric chloride induced thrombosis in rat carotid artery is compared to that achieved by clopidogrel. Compound A was administered by intravenous infusions and clopidogrel was dosed orally for three days. Ex vivo platelet aggregation induced by 10 μM ADP and clotting times (prothrombin time, PT and activated partial thromboplastin times, aPTT) were measured over the experimental time course (90 min) in all animals.

Table 2 shows that, when administered alone, Compound A produced a dose responsive inhibition of thrombosis as measured by the proportion of animals whose carotid artery does not occlude during the experiment. In particular, at 0.03 μM Compound A concentration a 30% inhibition of rat thrombosis (3 out of 10 tested animals did not occlude) was produced.

In control experiments using predosing of clopidogrel, a 1 mg/kg dose of antiplatelet agent was required to produce a 46% inhibition of ADP induced platelet aggregation in platelet rich plasma. This level of platelet inhibition is approximately equivalent to that attained by clopidogrel's effect on human platelets at the therapeutic dose in clinical use (75 mg per day). The corresponding level of inhibition of rat thrombosis is 89% (8 out of 9 tested animals did not occlude). At a sub-therapeutic dose of clopidogrel (0.01 mg/kg), only 10% of animals demonstrated effective antithrombotic activity (1 out of 10 animals did not occlude). Time to occlusion was measured in animals that had vessel occlusion.

As shown in Table 3, a combination of Compound A at 0.03 μM and clopidogrel at 0.01 mg/kg, both at sub-optimal doses, resulted in a 70% inhibition of rat thrombosis (7 out of 10 animals did not occlude), demonstrating a greater than additive antithrombotic effect. In addition, in the animals treated with Compound A and clopidogrel, markers of coagulation and platelet function such as PT and ADP induced platelet aggregation were minimally altered (5% and 7% respectively). This shows a lack of systemic perturbation of hemostasis which often leads to safety issues such as bleeding, and demonstrates that the combination's potential as a safer antithrombotic therapy than therapeutic doses of each single agent which produce significantly greater changes in the markers (33% and 46% respectively). Thus, this experiment shows that the combination of clopidogrel and Compound A possesses a superior activity than each of the single agents alone.

TABLE 2

| Concentration of Compound A | 0 | 0.03 μM | 0.1 μM | 0.3 μM |
|---|---|---|---|---|
| Number of animals | 20 | 10 | 10 | 10 |
| Number of animals without occlusion | 2 | 3 | 6 | 9 |
| % Did not occlude | 10 | 30 | 60 | 90 |
| time to occlusion | 29.82 | 27.07 | 52.66 | 35.78 |
| PT ratio | 1 | 1.08 | 1.19 | 1.33 |
| % inhibition of platelet aggregation | 0 | −2 | 4 | 0.8 |

TABLE 3

| | % Animals that did not occlude |
|---|---|
| Control | 10 |
| 0.03 μM Compound A | 30 |
| 0.01 mg/kg Clopidogrel | 10 |
| Combination treatment | 70 |

Example 6

Efficacy and Safety of Compound a for Prevention of Venous Thromboembolic Events after Total Knee Replacement In a prospective trial in the US and Canada, 215 patients undergoing total knee replacement (TKR) were randomized in a 2:2:1 ratio to either Compound A 15 mg or 40 mg oral twice a day or enoxaparin 30 mg subcutaneous twice a day for 10-14 days. The study was blinded to the 15 vs. 40 mg dose, but not to Compound A vs. Enoxaparin. The primary efficacy endpoint was the incidence of venous thromboembolism (VTE) (symptomatic or asymptomatic deep vein thrombosis on a mandatory unilateral venogram or symptomatic pulmonary embolism) through Days 10-14. Safety endpoints included the incidence of major and clinically significant nonmajor bleeds through the day after venography. All efficacy and bleeding endpoints were adjudicated by a blinded, independent central adjudication committee.

215 patients were randomized. A dose- and concentration-dependent effect of Compound A on inhibition of thrombin generation and anti-factor Xa levels was observed. 175 patients (81.4%) had an efficacy and safety assessment. These data are presented in Table 4, which show Compound A was effective in preventing VTE after TKR and was safe and well tolerated.

TABLE 4

Primary efficacy and safety outcomes

| | Compound A 15 mg bid (n = 69) | Compound A 40 mg bid (n = 65) | Enoxaparin 30 mg bid (n = 41) |
|---|---|---|---|
| VTE % (95% CI) | 20 (12-32) | 15 (8-27) | 10 (3-23) |
| Major Bleeds % | 0 (0-5) | 0 (0-6) | 2.3 (0-13) |
| Clinical significant nonmajor bleeds % | 0 (0-5) | 2.4 (0-11) | 4.5 (0-17) |

Example 7

Combination of Compound A and Low Molecular Weight Heparin Enoxaparin

Injectable heparins are often dose limited by their bleeding consequences which result in a narrow therapeutic window for treatment effects. Agents such as enoxaparin have reduced bleeding at doses used for prophylaxis of venous thromboembolic diseases (30 mg dosed subcutaneously, 0.4 mg/kg) but produce hemorrhagic side effects at doses which are used to treat acute coronary syndrome patients (1 mg/kg). As shown in Table 5, Compound A when dosed at supra-therapeutic doses (7 to 35 times greater than the 0.21 mg/kg to 0.57 mg/kg human therapeutic doses) did not extend of bleeding times in rhesus monkeys.

TABLE 5

Effect of Compound A on Template Bleed Times in Rhesus Monkeys

| Rhesus # | Compound A Dose | Time Point (hr) | | | | | | Mean | S.D. |
| | | 0 | 1 | 2 | 3 | 8 | 24 | | |
|---|---|---|---|---|---|---|---|---|---|
| 30675 | 4.0 (mg/kg) | 2.50 | 1.50 | 1.50 | 1.50 | 2.00 | 2.50 | 1.80 | 0.45 |
| 30973 | 4.0 (mg/kg) | 1.00 | 3.75 | 1.50 | 1.50 | 2.00 | 2.50 | 2.25 | 0.94 |
| | Mean | 1.75 | 2.63 | 1.50 | 1.50 | 2.00 | 2.50 | 1.98* | 2.03** |
| | S.D. | 1.06 | 1.59 | 0.00 | 0.00 | 0.00 | 0.00 | 0.74* | 0.73** |
| 25285 | 7.5 (mg/kg) | 3.00 | 3.00 | 2.50 | 2.50 | 4.00 | 2.50 | 2.90 | 0.65 |

TABLE 5-continued

Effect of Compound A on Template Bleed Times in Rhesus Monkeys

| Rhesus # | Compound A Dose | Time Point (hr) | | | | | | Mean | S.D. |
|---|---|---|---|---|---|---|---|---|---|
| | | 0 | 1 | 2 | 3 | 8 | 24 | | |
| 27678 | 7.5 (mg/kg) | 1.75 | 2.00 | 1.75 | 2.00 | 2.50 | 2.50 | 2.15 | 0.34 |
| | Mean | 2.38 | 2.50 | 2.13 | 2.25 | 3.25 | 2.50 | 2.50* | 2.53** |
| | S.D. | 0.88 | 0.71 | 0.53 | 0.35 | 1.06 | 0.00 | 0.63* | 0.63** |

*Mean/S.D. of all times
**Mean/S.D. for time points 1-24 hr (post-Compound A dosing).

Example 8

Combination of Compound A and Low Molecular Weight Heparin Enoxaparin

Ex vivo clotting assays were carried out in pooled human plasma to study the combination anticoagulant effect of Compound A and enoxaparin. Addition of a standard dose of low molecular weight heparin (0.5 U/mL enoxaparin, corresponding to the plasma concentration attained by a 30 mg dose) produced an activated partial thromboplastin time (aPTT) of 55 seconds. Addition of 10 nM or 15 nM of Compound A to the enoxaparin treated plasma provided an additional anticoagulant effect, as demonstrated by a 9 to 13% extension of aPTT values.

Example 9

Synergism of Compound A with Aspirin

An ex vivo assay system of human cytokine release was used to test whether inhibition of factor Xa should augment the effect of reduction of inflammation elicited by standard anti-inflammatory drugs, such as aspirin.

Whole blood from untreated (n=6) and aspirin treated (n=3) volunteer donors were drawn by venipuncture and collected in Vacutainer tubes under citrate (3.2%) anticoagulation. Following addition of Compound A (50 to 500 nM) to the blood samples, control and treated samples were activated by addition of collagen (Chronolog, 4 µg/mL) and gently rotated at 37° C. for 45 min. At the end of the activation period, blood samples were centrifuged at 13,000 rpm (15,000 g) for 5 min in an Eppendorf 5415G centrifuge. Plasma was removed, treated with protease inhibitor cocktail (Roche) and stored frozen at −80° C. Cytokines released from the blood cells were quantitated in a Multiplexed Biomarker Immunoassay for Luminex Instrumentation (Millipore USA). Representative results for two cytokines (interleukin 6 and 8) are shown in Tables 6 and 7. When blood samples for healthy donors were treated with Compound A, the single treatment did not produce statistically significant inhibition of cytokine release in the blood samples. For example, in the plasma samples from six donors, the mean amount of interleukin 4 was 28.4 pg/mL in the untreated control and 26.8 to 29.4 pg/mL in the Compound A treated samples. Surprisingly, when Compound A was added to the blood samples from donors under aspirin therapy, a reduction in the levels of released cytokines such as interleukins 6 and 8 (25% and 44% respectively) was observed. Moreover, addition of Compound A to whole blood prior to collagen activation resulted in further reduction of interleukins 6 and 8 of 16% and 18%, respectively. Thus in this ex vivo system Compound A was capable of providing additional beneficial effect over a widely used anti-inflammatory agent.

TABLE 6

Effect of combination treatment by Compound A and Aspirin on the Release of a Cytokine, Interleukin 6, in Human Whole Blood

| Compound A Concentration (nM) | fold change | Standard Deviation | Standard Error of the Mean |
|---|---|---|---|
| 0 | 1 | — | — |
| 50 | 1.01 | 0.11 | 0.08 |
| 200 | 0.96 | 0.11 | 0.06 |
| 500 | 0.87 | 0.06 | 0.03 |

TABLE 7

Effect of Combination Treatment by Compound A and Aspirin on the Release of a Cytokine, Interleukin 8, in Human Whole Blood

| | # of donors | Percent Release of IL8 |
|---|---|---|
| Control | 6 | 100.0 |
| Control + ASA | 3 | 66.7 |
| ASA + 50 nM Compound A | 2 | 73.0 |
| ASA + 200 nM Compound A | 3 | 60.0 |
| ASA + 500 nM Compound A | 3 | 55.0 |

Example 10

Combination of Compound A and Verapamil

The study was designed to evaluate the in vivo effect of Compound A upon co-administration with a selective L type calcium channel blocker, verapamil. Three beagle dogs were implanted with Data Science Telemetry transmitters (DSI model # TL11M2-D70-PCT) to measure conscious (un-anaesthetized) and unrestrained systolic and diastolic blood pressure following oral dosing with Compound A, verapamil or a combination of the two. The study design was a three way crossover with one week between doses to ensure complete elimination of residual agents from the dogs' circulatory system. Data was analyzed for a twelve hour period, starting with one hour pre-oral dosing of Compound A and ending with eleven hours post-dosing. Data acquisition and analysis was performed using LDS Life Science Suite Ponemah P3 plus V 4.20 software with results reported as 10 minute averages for each animal.

Administration of Compound A (3 mg/kg) as a single agent showed no statistical differences in diastolic blood pressure (DBP) compared to pre-dose values over the course of the experiment. Verapamil (10 mg/kg) as a single agent decreased diastolic blood pressure by 33% within one hour of oral administration. Area under the curve quantitation of DBP for verapamil alone (−3079±1846 mmHg*min) was statistically lower than the Compound A group (448±161 mmHg*min)

(p<0.05). The combination treatment (Compound A and verapamil) produced similar results to the verapamil as a single agent group with a DBP area under the curve of −3157±450 mmHg*min. Results are shown in Tables 8 and 9. The experiments also illustrated that Compound A can be safely combined with a blood pressure lowering agent.

TABLE 8

Lowest Systolic and Diastolic Blood Pressure Post-Dosing of Compound A and Verapamil
Systolic and Diastolic Blood Pressure (mmHg)

| Blood Pressure | Dose | Dog # 1 | 2 | 3 | Mean ± S.D. |
|---|---|---|---|---|---|
| Systolic | Compound A alone | 150.32 | 121.08 | 101.93 | 124.44 ± 24.37 |
| | Verapamil alone | 137.18 | 111.90 | 95.52 | 114.87 ± 20.99 |
| | Compound A + Verapamil | 127.97 | 111.43 | 109.98 | 116.46 ± 9.99 |
| Diastolic | Compound A alone | 92.57 | 83.73 | 80.52 | 85.60 ± 6.24 |
| | Verapamil alone | 65.11 | 62.47 | 51.94 | 59.84 ± 6.97[1] |
| | Compound A + Verapamil | 61.33 | 53.00 | 59.12 | 57.82 ± 4.31[1] |

[1]Statistically reduced compared to Compound A alone, p < 0.05 (Bonferroni t-test). No statistical difference observed between Verapamil alone and Compound A + Verapamil.

Area under the curve (AUC) was calculated from verapamil or placebo dosing to approximately 4.5 hrs post-dosing. AUC was derived from the systolic and diastolic baseline. Baseline values were the mean blood pressure observed from Compound A or Vehicle to Verapamil dosing. Negative values represent a decrease in blood pressure relative to the baseline value.

TABLE 9

Mean Area Under the Curve for Systolic and Diastolic Pressure (AUCP) Following Verapamil or Placebo Administration (4.5 hrs)

| Blood Pressure | Agent(s) | AUCP (mmHg * min.) Mean ± S.D. |
|---|---|---|
| Systolic | Compound A | 782.7 ± 1297.8 |
| | Verapamil | −1133.6 ± 1134.7 |
| | Compound A + Verapamil | 389.6 ± 666.8 |
| Diastolic | Compound A | 447.5 ± 160.5 |
| | Verapamil | −3077.8 ± 1845.51 |
| | Compound A + Verapamil | −3156.4 ± 449.71 |

[1]Statistically reduced compared to Compound A, p < 0.05 (Bonferroni t-test). No statistical difference observed between Verapamili and Compound A + Verapamil (p = 1.00).

Example 11

Combination of Compound A and Aspirin in Thrombin Generation Assay in Platelet Rich Plasma (PRP)

Human platelet poor plasma (PPP) or platelet rich plasma (PRP) was prepared from blood of healthy donors drawn into 0.32% citrate. PRP and PPP were prepared by spinning the anticoagulated blood at ~100×g or 1000×g for 20 minutes, respectively, at room temperature. Platelet counts in PRP were adjusted with homologous PPP to about 200,000 platelets/µL. For thrombin generation in 100 µL reaction mixture, 75 µL PRP was first mixed with $CaCl_2$, convulxin, and Z-Gly-Gly-Arg-aminomethylcoumarin (Z-GGR-AMC, a thrombin fluorogenic substrate) for 3 minutes at 37° C., followed by adding tissue factor (Innovin, Dade Behring) to initiate the generation of thrombin. A typical reaction mixture contained 15 mM $Ca^{2+}$, 0.1 µg/mL convulxin, 100 µM Z-GGR-AMC, and 0.1 nM TF (tissue factor) (Innovin). Thrombin formation was monitored continuously at 37° C. by a fluorometric plate reader (Molecular Devices) measuring the relative fluorescence units (RFU). Inhibitors were pre-incubated with plasma for 20 minutes at room temperature before adding $CaCl_2$ and convulxin.

Table 10 shows the effect of a combination of Compound A and aspirin on thrombin generation (n=5) in terms of percent inhibition (% Inhibition). Non-ASA represents result from donors free of aspirin. ASA represents results from donors taken aspirin for at least three days. % Inhibition was calculated by normalization of mean RFU (n=5) to Non-ASA at 0 nM Compound A.

TABLE 10

| Compound A Concentration (nM) | % Inhibition | |
|---|---|---|
| | Non-ASA | ASA |
| 0 | 0.0 | 21.5 |
| 7.8125 | 3.2 | 24.6 |
| 15.625 | 5.1 | 26.9 |
| 31.25 | 12.2 | 33.4 |
| 62.5 | 25.2 | 46.0 |
| 125 | 55.1 | 64.7 |
| 250 | 81.1 | 82.5 |
| 500 | 96.0 | 94.6 |

Example 12

Combination of Compound A and Aspirin, an Anti-Platelet Agent

The combination effect of an anticoagulant and anti-platelet agent, aspirin, was investigated in an in vivo model of thrombosis. This well characterized animal model (Lockyer and Kambayashi, Demonstration of Flow and Platelet Dependency in a Ferric Chloride Induced Model of Thrombosis, *J. Cardiovasc. Pharmacol.* 1999, 33(5):718-25) has been previously used to test both anticoagulants and antiplatelet agents. In this experiment, the ability of Compound A to maintain vessel patency under arterial flow conditions in ferric chloride induced thrombosis in rat carotid artery is compared to that achieved by aspirin. Compound A was administered by intravenous infusions and aspirin was administered as an intravenous bolus approximately 30 min prior to the start of the experiment. Ex vivo platelet aggregation induced by 10 µg/mL of collagen and clotting times (prothrombin time, PT and activated partial thromboplastin times, aPTT) were measured over the experimental time course (90 min) in all animals.

Compound A, when administered alone, produced a dose responsive inhibition of thrombosis as measured by the proportion of animals whose carotid artery does not occlude during the experiment. Compound A at plasma concentrations of 0.03, 0.1, and 0.3 µM produced a 30, 60, and 90% inhibition of rat thrombosis, respectively. For comparison, 3 out of 32 vehicle control animals did not occlude during the experiment yielding a 9.4% inhibition of thrombosis in the rat.

In experiments with aspirin, a 3 mg/kg dose produced a 35% inhibition of collagen induced platelet aggregation in platelet rich plasma. The corresponding level of inhibition of thrombosis was 30% (3 out of 10 tested animals did not occlude). Increasing the aspirin dose to 10 mg/kg more than doubled the % inhibition of collagen induced platelet aggregation (77%), but, had a minimal effect on increasing the level of inhibition of rat thrombosis (33.3% or 3 out of 9 tested animals did not occlude). At a lower dose of aspirin (1.0 mg/kg), antithrombotic activity was similar to vehicle control levels as demonstrated in only 10% of the animals (1 out of 10 animals did not occlude). At the low dose of aspirin, collagen induced platelet aggregation was only slightly inhibited (<2%).

As shown in Table 11, a combination of Compound A at 0.03 µM and aspirin at 3 mg/kg resulted in a 40% inhibition of rat thrombosis (4 out of 10 animals did not occlude), demonstrating a slight additive antithrombotic effect. In addition, in the animals treated with Compound A and aspirin, coagulation markers (PT) were not different from Compound A alone results. This demonstrates a lack of systemic perturbation of hemostasis which often leads to safety issues such as bleeding, and demonstrates that the combination has potential as a safer therapy to achieve a greater antithrombotic effect than therapeutic doses of each single agent. Thus, this experiment shows that the combination of aspirin and Compound A possesses a superior activity than each of the single agents alone.

TABLE 11

| Dose | n | DNO | % DNO | TTO (min.) | PT Ratio | APTT Ratio |
|---|---|---|---|---|---|---|
| Control | 32 | 3 | 9.4% | 28.78 ± 9.81 | 1.00 | 1.00 |
| Compound A | 10 | 3 | 30% | 27.07 ± 7.36 | 1.07 | 1.08 |
| 3 mg/kg aspirin | 10 | 3 | 30% | 31.61 ± 10.91 | 1.01 | 1.02 |
| Combination | 10 | 4 | 40% | 39.03 ± 23.41 | 1.07 | 1.01 |

DNO = did not occlude
TTO = Time to occlusion. Average time to occlusion for animals that occluded.

Example 13

Lower Concentrations of Compound A are Needed to Inhibit Mesenteric Artery Thrombosis in Mice which Express Reduced Levels of $P2Y_{12}$ Receptor Commonly used $P2Y_{12}$ antagonists such as clopidogrel are prescribed at doses that block 40-50% of the $P2Y_{12}$ receptors on platelets of treated patients. It has been shown that $P2Y_{12}^{+/-}$ mice which express ~50% of the receptor on their platelets compared to wild type control ($P2Y_{12}^{+/+}$), display an intermediate thrombosis phenotype between wild type and mice completely deficient in $P2Y_{12}$ ($P2Y_{12}^{-/-}$). (Andre, P., et al., J Clin Invest, 2003. 112(3):398-406). $P2Y_{12}$ regulates platelet adhesion/activation, thrombus growth, and thrombus stability in injured arteries. The effect of Compound A was studied in a thrombosis model with $P2Y_{12}^{+/-}$ mice to effectively mimic the combination of dual dosing of factor Xa inhibitor and $P2Y_{12}$ antagonist in humans.

Thrombosis on mouse mesenteric arteries (shear rate 1000-1300 $s^{-1}$) was performed and recorded as previously described (Andre, P., et al., J Clin Invest, 2003. 112(3):398-406). Platelets were labeled in situ using rhodamine 6G (0.2 mg/mL) and administered through the tail vein 10 min before visualization of the arteries. Vessel-wall injury was triggered by a 1×1-mm filter paper saturated with a 10% $FeCl_3$ solution. After 5 minutes, the filter paper was removed and mesenteric arteries rinsed with warmed saline (37° C.). Platelet vessel-wall interactions were recorded for 40 additional minutes or until full occlusion occurred and persisted for more than 40 seconds. C57Bl6J mice (wild type control or $P2Y_{12}^{+/-}$) were orally gavaged with vehicle control, compound A (2, 4, 10 mg/kg) two hours prior to vascular injury. Thrombosis was analyzed in real time using Simple PCI software. The fluorescence intensity was recorded at a rate of 2 Hz for 40 minutes and plotted over time. Time to occlusion (cessation of blood flow) was analyzed. Plasma concentrations of Compound A were determined on blood collected 2 min post-occlusion or 42 min after start of vascular injury.

In wild type controls, doses of 2 and 4 mg/kg Compound A were non-effective whereas doses of 10 mg/kg significantly delayed both time for appearance of first thrombus and time to occlusion. Circulating plasma concentrations of more than 1000 ng/mL of Compound A prevented vascular occlusion in wild type animals. In contrast, a concentration of more than 76 ng/mL was sufficient to prevent vascular occlusion in $P2Y_{12}^{+/-}$ animals. We also observed potent synergistic antithrombotic activity by combining modulation of $P2Y_{12}$ activity with inhibition of factor Xa by Compound A. As shown in Table 12, reduced $P2Y_{12}$ activity extends time to occlusion from a baseline of 368 sec to 756.7 seconds. Additional inhibition upon addition of Compound A, produces a substantial extension of time to occlusion (756.7 seconds to over 2100 seconds), illustrating the enhanced efficacy of dual inhibition.

TABLE 12

| | $P2Y_{12}^{+/-}$ Compound A (10 mg/kg) Experiment 1 | $P2Y_{12}^{+/-}$ Compound A (10 mg/kg) Experiment 2 | $P2Y_{12}^{+/-}$ Compound A (10 mg/kg) Experiment 3 | $P2Y_{12}^{+/-}$ No fXa inhibitor | $P2Y_{12}^{+/+}$ No fXa inhibitor |
|---|---|---|---|---|---|
| Number of animals | 4 | 5 | 5 | 6 | 9 |
| Mean time to occlusion (sec) | 2143 | 2399 | 2305 | 756.7 | 368.1 |
| Std. Deviation | 552.1 | 674 | 573.7 | 273.9 | 73.37 |
| Std. error of the mean | 276.1 | 301.4 | 256.6 | 111.8 | 24.46 |

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for treating a condition in a mammal characterized by undesired thrombosis comprising administering to said mammal a therapeutically effective amount of
    (1) [2-({4-[(dimethylamino)iminomethyl]phenyl}carbonylamino)-5-methoxyphenyl]-N-(5-chloro(2-pyridyl))carboxamide, of the formula:

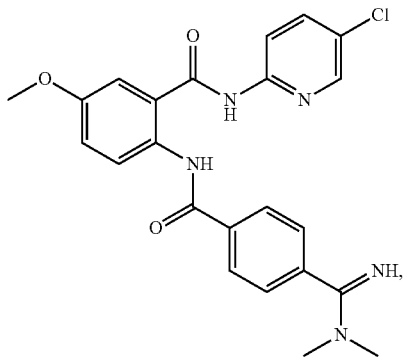

or a pharmaceutically acceptable salt thereof; and
    (2) a $P2Y_{12}$ receptor antagonist.

2. The method of claim 1, wherein the $P2Y_{12}$ receptor antagonist is selected from the group consisting of cangrelor, ticagrelor, clopidogrel, ticlopidine, and prasugrel.

3. The method of claim 2, wherein the $P2Y_{12}$ receptor antagonist is clopidogrel.

4. The method of claim 1, wherein at least one of [2-({4-[(dimethylamino)iminomethyl]phenyl}carbonylamino)-5-methoxyphenyl]-N-(5-chloro(2-pyridyl))carboxamide, or a pharmaceutically acceptable salt thereof, and the $P2Y_{12}$ receptor antagonist is administered in a sub-therapeutic dosage.

5. The method of claim 1, wherein both of [2-({4-[(dimethylamino)iminomethyl]phenyl}carbonylamino)-5-methoxyphenyl]-N-(5-chloro(2-pyridyl))carboxamide, or a pharmaceutically acceptable salt thereof, and the $P2Y_{12}$ receptor antagonist are administered in sub-therapeutic dosages.

6. The method of claim 1, wherein [2-({4-[(dimethylamino)iminomethyl]phenyl}carbonylamino)-5-methoxyphenyl]-N-(5-chloro(2-pyridyl))carboxamide, or a pharmaceutically acceptable salt thereof, and the $P2Y_{12}$ receptor antagonist are administered simultaneously.

7. The method of claim 1, wherein [2-({4-[(dimethylamino)iminomethyl]phenyl}carbonylamino)-5-methoxyphenyl]-N-(5-chloro(2-pyridyl))carboxamide, or a pharmaceutically acceptable salt thereof, and the $P2Y_{12}$ receptor antagonist are administered sequentially.

8. The method of claim 1, wherein the pharmaceutical acceptable salt of [2-({4-[(dimethylamino)iminomethyl]phenyl}carbonylamino)-5-methoxyphenyl]-N-(5-chloro(2-pyridyl))carboxamide is the maleate salt.

9. The method of claim 1, wherein the method further comprises administering to said mammal a therapeutically effective amount of:
    (3) a third therapeutic agent selected from an antiplatelet agent, an anticoagulant agent, a thrombin inhibitor, a thrombolytic agent, an anti-arrhythmic agent, a blood pressure lowering agent, a cholesterol or triglyceride lowering agent.

10. The method of claim 1, wherein the condition is selected from the group consisting of:
    acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

11. A pharmaceutical composition, comprising two therapeutic agents:
    (1) [2-({4-[(dimethylamino)iminomethyl]phenyl}carbonylamino)-5-methoxyphenyl]-N-(5-chloro(2-pyridyl))carboxamide, of the formula:

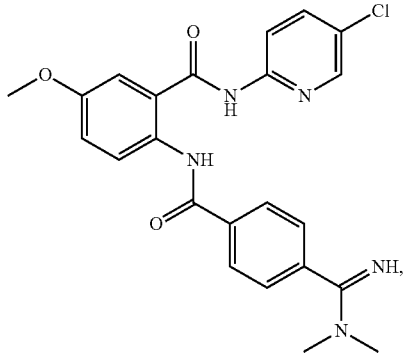

or a pharmaceutically acceptable salt thereof;

(2) a P2Y$_{12}$ receptor antagonist; and
a pharmaceutically acceptable carrier.

12. The pharmaceutical composition of claim 11, wherein the P2Y$_{12}$ receptor antagonist is selected from the group consisting of cangrelor, ticagrelor, clopidogrel, ticlopidine, and prasugrel.

13. The pharmaceutical composition of claim 12, wherein the P2Y$_{12}$ receptor antagonist is clopidogrel.

14. The pharmaceutical composition of claim 11, wherein at least one of the therapeutic agents is present in a sub-therapeutic dosage.

15. The pharmaceutical composition of claim 11, wherein both of the therapeutic agents are present in sub-therapeutic dosages.

16. The pharmaceutical composition of claim 11, wherein the pharmaceutical acceptable salt of [2-({4-[(dimethylamino)iminomethyl]phenyl}carbonylamino)-5-methoxyphenyl]-N-(5-chloro(2-pyridyl))carboxamide is the maleate salt.

17. The pharmaceutical composition of claim 11, further comprising:
(3) a third therapeutic agent selected from an antiplatelet agent, an anti-coagulant, a thrombin inhibitor, a thrombolytic agent, an anti-arrhythmic agent, a blood pressure lowering agent, a cholesterol or triglyceride lowering agent.

18. A kit, comprising:
(1) a first container, wherein said container comprises [2-({4-[(dimethylamino)iminomethyl]phenyl}carbonylamino)-5-methoxyphenyl]-N-(5-chloro(2-pyridyl))carboxamide, of the formula:

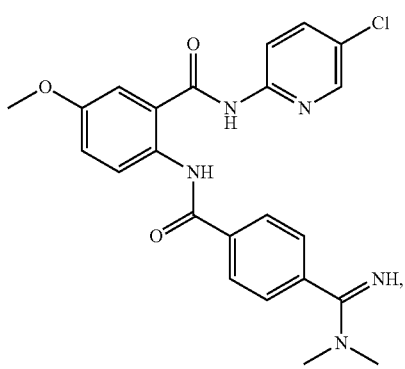

or a pharmaceutically acceptable salt thereof; and
(2) a second container, wherein said container comprises a P2Y$_{12}$ receptor antagonist.

19. The kit of claim 18, further comprising:
(3) a package insert stating that the two therapeutic agents can be used together.

20. The kit of claim 18, wherein the pharmaceutically acceptable salt of [2-({4-[(dimethylamino)iminomethyl]phenyl}carbonylamino)-5-methoxyphenyl]-N-(5-chloro(2-pyridyl))carboxamide is the maleate salt.

21. The kit of claim 18, wherein at least one of the therapeutic agents is present in a sub-therapeutic dosage.

22. The kit of claim 18, wherein both of the therapeutic agents are present in sub-therapeutic dosages.

23. The kit of claim 18, wherein the P2Y$_{12}$ receptor antagonist is selected from the group consisting of cangrelor, ticagrelor, clopidogrel, ticlopidine, and prasugrel.

24. The kit of claim 18, wherein the P2Y$_{12}$ receptor antagonist is clopidogrel.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Pro Arg Pro
1